United States Patent
Akiyama et al.

(10) Patent No.: US 9,746,662 B2
(45) Date of Patent: Aug. 29, 2017

(54) ENDOSCOPE OBSERVATION SYSTEM

(75) Inventors: Daisuke Akiyama, Hino (JP); Takeshi Suga, Hino (JP)

(73) Assignee: OLYMPUS CORPORATION, Tokyo (JP)

(*) Notice: Subject to any disclaimer, the term of this patent is extended or adjusted under 35 U.S.C. 154(b) by 1718 days.

(21) Appl. No.: 12/400,766

(22) Filed: Mar. 9, 2009

(65) Prior Publication Data
US 2009/0225156 A1 Sep. 10, 2009

(30) Foreign Application Priority Data
Mar. 10, 2008 (JP) .................. 2008-059911

(51) Int. Cl.
*A61B 1/04* (2006.01)
*G02B 23/24* (2006.01)
(Continued)

(52) U.S. Cl.
CPC ...... *G02B 23/2469* (2013.01); *A61B 1/00096* (2013.01); *A61B 1/00186* (2013.01);
(Continued)

(58) Field of Classification Search
CPC .......... G02B 23/2469; G02B 5/285; G02B 27/1006; G02B 27/283; A61B 1/00096;
(Continued)

(56) References Cited

U.S. PATENT DOCUMENTS 6,118,476 A * 9/2000 Morito et al. .................. 348/65
2003/0040668 A1* 2/2003 Kaneko et al. ............... 600/407
(Continued)

FOREIGN PATENT DOCUMENTS

| JP | H9-294706 | 11/1997 |
|---|---|---|
| JP | 2003-047588 | 2/2003 |

(Continued)

OTHER PUBLICATIONS

Vadim Backman, et al., "Polarized Light Scattering Spectroscopy for Quantitative Measurement of Epithelial Cullular Structures in Situ", IEEE Journal of Selected Topics in Quantum Electronics, vol. 5, No. 4, Jul./Aug. 1999, pp. 1019-1026.
(Continued)

*Primary Examiner* — Joseph Greene
(74) *Attorney, Agent, or Firm* — Andrews Kurth Kenyon LLP

(57) ABSTRACT

An endoscope observation system includes a light source section generating different types of light in at least partly different wavelength bands for observation of a polarized light-based observation image and for observation of a non polarized light-based observation image, respectively; an irradiation side polarization separation element subjecting the illumination light from the light source section to polarization separation; a light reception side polarization separation element performing polarization separation, in a particular wavelength band of the light from the observation target, by transmitting polarized light with a predetermined polarization component while reflecting polarized light with a polarization component other than the predetermined polarization component, and in a wavelength bend other than the particular wavelength band, exhibiting same transmission and reflection characteristics for both polarized light and non polarized light; and an image pickup element receiving the transmitted or reflected light.

17 Claims, 12 Drawing Sheets

(51) Int. Cl.
  *A61B 1/00*  (2006.01)
  *A61B 1/05*  (2006.01)
  *A61B 1/06*  (2006.01)
  *A61B 5/00*  (2006.01)
  *G02B 5/28*  (2006.01)
  *G02B 27/10*  (2006.01)
  *G02B 27/28*  (2006.01)

(52) U.S. Cl.
  CPC .............. *A61B 1/05* (2013.01); *A61B 1/0638* (2013.01); *A61B 1/0646* (2013.01); *A61B 5/0084* (2013.01); *G02B 5/285* (2013.01); *G02B 27/1006* (2013.01); *G02B 27/283* (2013.01)

(58) Field of Classification Search
  CPC ..... A61B 1/00186; A61B 1/05; A61B 1/0638; A61B 1/0646; A61B 5/0084
  USPC ...................................... 348/65, 68
  See application file for complete search history.

(56) References Cited

U.S. PATENT DOCUMENTS

| | | | | |
|---|---|---|---|---|
| 2004/0246874 | A1* | 12/2004 | Takagi et al. | 369/112.15 |
| 2005/0243314 | A1* | 11/2005 | Chinnock | 356/364 |
| 2007/0211255 | A1* | 9/2007 | Ohkubo | 356/479 |
| 2007/0237445 | A1* | 10/2007 | Hatori | 385/11 |
| 2008/0007834 | A1 | 1/2008 | Atsuta et al. | |
| 2008/0027286 | A1* | 1/2008 | Xie | 600/181 |

FOREIGN PATENT DOCUMENTS

| | | |
|---|---|---|
| WO | WO 00/42912 | 7/2000 |
| WO | WO 02/075316 | 9/2002 |

OTHER PUBLICATIONS

A.G. Harris, et al., "The Study of the Microcirculation Using Orthogonal Polarization Spectral Imaging", Yearbook of Intensive Care and Emergency Medicine 2000, pp. 706-714.

* cited by examiner

ENDOSCOPE OBSERVATION SYSTEM

This application claims benefits of Japanese Patent Application No. 2008-059911 filed in Japan on Mar. 10, 2008, the contents of which are hereby incorporated by reference.

BACKGROUND OF THE INVENTION

1. Field of the Invention

The present invention relates to an endoscope observation system that allows observation of polarized images obtained using polarized light and normal images obtained using normal light.

2. Description of the Related Art

An endoscope is conventionally known as an optical device with which the interior of a living body to be diagnosed and/or treated is observed. In general, when the appearance, shape, or the like of interior of the living body is observed using the endoscope, non polarized light is used as observation light. Illumination light is emitted to an observation target site via an illumination optical system provided inside a distal end portion of the endoscope inserted into the living body. Light from the observation target site is received by an image pickup optical system provided inside the distal end portion of the endoscope. An image pickup element then picks up an image from the light. The picked-up image is displayed on an image display device or the like.

The endoscope may be effectively used in observation using polarized light for diagnosis of, for example, HGD and an early cancer, in addition to the observation using the non polarized light. The HGD, early cancer, and the like are developed in proximity to the surface of living tissues. It is known that extracting and analyzing scattering light only from the tissue surface allows the nature of the tissues to be determined to find an abnormal tissue and that polarized light can be effectively used to extract the scattering light only from the tissue surface, as described in PCT WO 00/42912. Furthermore, polarization of light scattering inside the tissue is disturbed. The abnormal tissue such as the early cancer or the like has large cell nuclei. Consequently, the level of scattering inside the abnormal tissue is different from that inside the normal tissue. Thus, the abnormality of the interior of the tissue can be estimated by measuring the level of scattering of the polarized light (the level of disturbance of the polarized light) having entered the tissue.

PCT WO 00/42912 discloses a device shown in FIG. 1. FIG. 1 is cited from IEEE JOURNAL OF SELECTED TOPICS IN QUANTUM ELECTRONICS VOL. 5, NO. 4, p. 1010-1026, which is authored by the inventor of PCT WO 00/42912. In the device 50, shown in FIG. 1, white light from a broadband light source 51 is guided through fibers 52 and converted into particular linearly polarized light through a lens 53, an aperture stop 54, and a polarizer 55. The linearly polarized light then enters a beam splitter 56. Light reflected by the beam splitter 56 impinges on a living tissue 57. The light is then scattered in the living tissue 57 and enters a beam splitter 56. Part of the light passes through the beam splitter 56 and then through an aperture stop 58. The part of the light is reflected by a mirror 59 and then enters a polarization beam splitter 60.

A light component of the light having entered the polarization beam splitter 60 passes through the polarization beam splitter 60; the light component has a polarization direction that is parallel to a direction in which light is polarized by the polarizer 55. The light component is guided to a multi-channel spectroscope 62 via a lens 61a or the like. A light component having a polarization direction that is orthogonal to the polarization direction of the polarizer 55 is reflected by the polarization beam splitter 60 and then guided to the multi-channel spectroscope 62 via a lens 61b or the like. The beam splitter 56 is located such that the illumination light slightly obliquely enters the living tissue 57 so as to prevent the reflected light from the living tissue 57 from directly entering the spectroscope 62. The parallel and perpendicular components separated from the incident light by the polarization beam splitter 60 enter the spectroscope 62. The spectroscope 62 subjects the components to background correction (the ratio of each of the components to a scatterer of white light is determined) and then determines the difference between the components.

This configuration irradiates the living tissue 57 with the light with the particular polarization component and divides the resultant scattering light into the polarization components that are parallel and perpendicular, respectively, to the polarization component of the irradiation light to detect spectrum. In this case, the scattering light returning from the surface of the living tissue 57 contains the polarization component that is parallel to the polarization component of the irradiation light. On the other hand, scattering light returning from a deep portion of the living tissue 57 has been intensely scattered. Thus, the scattering light contains equivalent quantities of the polarization component that is parallel to that of the irradiation light and the polarization component that is perpendicular to that of the irradiation light. Thus, the scattering light with the parallel polarization component contains both the component of the light from the surface of the living tissue 57 and the component of the light from the deep portion of the living tissue 57. The scattering light with the perpendicular polarization component contains the component of the light from the deep portion of the living tissue 57.

Here, the scattering light from the surface of the living tissue 57 can be exclusively extracted by determining the difference between the scattering light with the parallel polarization component and the scattering light with the perpendicular polarization component. Moreover, the sizes of the cell nuclei can be estimated by analyzing the spectrum of the scattering light from the surface of the living tissue 57. Thus, the use of the polarization allows the scattering light containing information on the sixes of the nuclei to be extracted at a high S/N ratio.

Besides PCT WO 00/42312, A. Harris et al., The Study of the Microcirculation using Orthogonal Polarization Spectral Imaging, Yearbook of Intensive Care and Emergency Medicine 2000 discloses a method of improving the contrast of a vessel image using polarization. Specifically, a tissue is irradiated with light with a particular polarization component. Scattering light is imaged which has a polarization component perpendicular to the polarization component of the irradiation light. In this case, the scattering light returning from the surface of the tissue contains the polarization component that is parallel to the polarization component of the irradiation light. On the other hand, scattering light returning from a deep portion of the tissue has been intensely scattered. Thus, the scattering light contains equivalent quantities of the polarization component that is parallel to that of the irradiation light and the polarization component that is perpendicular to that of the irradiation light. That is, the scattering light from the deep portion of the tissue can be imaged by imaging the light with the polarization component that is perpendicular to that of the irradiation light. This reduces the scattering light from the tissue surface, thus making an observer feel that the observer is directly viewing light from the deep portion of the tissue. The contrast of the vessel in the tissue surface can thus be improved.

As described above, for the endoscope, the observation using the polarization is expected to be more effective for determining the presence or absence of a lesion and/or diagnosis than the conventional observation with the non polarized light, for example, the observation with the normal light such as visible light. For example, Japanese Patent Laid-Open No. 2003-47588 describes a conventional endoscope observation system that provides observation images using the non polarized light such as the normal light, while providing polarized images utilizing the polarized light. FIG. 2 schematically shows the configuration of an endoscope observation system described in Japanese Patent Laid-Open No. 2003-47588. The endoscope observation system described in Japanese Patent Laid-Open No. 2003-47588 has a light source section 71, an endoscope 72 including an illumination optical system 72a and an image pickup optical system 72b, an image processing device 73, and an image display device 74.

The light source section 71 is configured to be able to emit illumination light for normal observation which allows observation images to be obtained using the normal light and illumination light for polarization observation which has a plurality of wavelength bands and which allows observation images to be obtained using the polarized light. The illumination optical system 72a also includes a polarizer $72a_1$ that polarizes the light from the light source section 71. The image pickup optical system 72b includes a polarization beam splitter $72b_1$ as a polarization separation element, and image pickup elements $72b_{21}$ and $72b_{22}$ on respective optical paths separately formed by the polarization separation element. The image processing device 73 executes predetermined image processing on image data picked up by the image pickup elements $72b_{21}$ and $72b_{22}$. The image display device 74 displays images processed by the image processing device 73. Switching the light emitted by the light source section 71 allows observation images to be obtained using the normal light or the polarized light. For normal observation, two polarized images separately formed by the polarization separation element $72b_1$ are synthesized via the image processing device 73.

As described above, to allow observation of the polarization condition of reflected light obtained when an observation target is irradiated with polarized light, the polarization separation element needs to be provided in the optical path in the image pickup optical system in order to obtain a polarized image. Furthermore, to allow observation of scattering light information on the mucosa using polarized light, the polarization separation element also needs to be provided in the optical path in the image pickup optical system in order to allow the following operation to be performed. As described above, the mucosa is irradiated with polarized light, and son polarized light is obtained which is a mixture of light returning from the mucosa and maintaining the polarized condition and light also returning from the mucosa but having the polarization condition disturbed. Then, the following images are picked up: an image (non polarized image) of the non polarized light, and an image (polarized image) of a particular polarization component extracted from the non polarized light. The difference between the images is then determined for analysis.

SUMMARY OF THE INVENTION

An endoscope observation system according to the present invention is configured to allow a polarized light-based observation image and a non polarized light-based observation image to be observed, and includes a light source section generating different types of illumination light in at least partly different wavelength bands for observation of the polarized light-based observation image and for observation of the non polarized light-based observation image, an irradiation side polarization separation element provided on an irradiation side optical path through which an observation target is irradiated with the illumination light from the light source section, the irradiation side polarization separation element subjecting the illumination light from the light source section to polarization separation, a light reception side polarization separation element provided on a light reception side optical path through which light from the observation target is received, the light reception side polarization separation element performing polarization separation, in a particular wavelength band of the light from the observation target, by transmitting polarized light with a predetermined polarization component while reflecting polarized light with a polarization component other than the predetermined polarization component, and in a wavelength band other than the particular wavelength band, exhibiting same transmission and reflection characteristics for both polarized light and non polarized light, and an image pickup element receiving the light transmitted through or reflected by the light reception side polarization separation element.

Furthermore, in the endoscope observation system according to the present invention, preferably, the irradiation side polarization separation element performs polarization separation, in a particular wavelength band of the illumination light from the light source section, by transmitting polarized light with a predetermined polarization component while reflecting polarized light with a polarization component other than the predetermined polarization component, and in a wavelength band other than the particular wavelength band, exhibits same transmission and reflection characteristics for both polarized light and non polarized light.

Furthermore, in the endoscope observation system according to the present invention, preferably, in a polarization separation wavelength band, each of the irradiation side polarization separation element and the reception side polarization separation element separates the illumination light into two orthogonal rays of linearly polarized light.

Furthermore, in the endoscope observation system according to the present invention, preferably, each of the irradiation side polarization separation element and the reception side polarization separation element is of a prism type.

Furthermore, in the endoscope observation system according to the present invention, preferably, the irradiation side polarization separation element and the reception side polarization separation element are arranged such that in the polarization separation wavelength band, a polarization direction of the polarization component transmitted by the irradiation side polarization separation element is orthogonal to a polarization direction of the polarization component transmitted by the reception side polarization separation element.

Furthermore, in the endoscope observation system according to the present invention, preferably, each of the irradiation side polarization separation element and the reception side polarization separation element has a boundary wavelength. The boundary wavelength which separates a transmission wavelength band and the polarization separation wavelength band is longer than 580 nm.

Furthermore, in the endoscope observation system according to the present invention, preferably, the illumination light used to observe the polarized light-based observation image comprises two types of light in different wavelength bands.

Furthermore, the endoscope observation system according to the present invention preferably further includes an image processing device calculating image information obtained by allowing the image pickup element to pick up an image of light in one of the two different wavelength bands and image information obtained by allowing the image pickup element to pick up an image of light in the other wavelength band, to synthesize the image information into one image.

Furthermore, in the endoscope observation system according to the present invention, preferably, the wavelength of the illumination light used to observe the polarized light-based observation image is longer than 580 nm.

The present invention provide an endoscope observation system which allows the observation based on the non polarized light such as the normal light and the polarized light-based observation to be substantially simultaneously performed using the same image pickup optical system without the need for a mechanical structure for switching the polarization member, while preventing an increase in diameter and minimizing a decrease in the quantity of light for the non polarized light-based observation, the endoscope observation system being used for the polarization observation to enable the image corresponding to the difference between the image of the non polarization component and the image of the polarization component to be substantially simultaneously acquired.

These and other features and advantages of the present invention will become apparent from the following detailed description of the preferred embodiments when taken in conjunction with the accompanying drawings.

BRIEF DESCRIPTION OF THE DRAWINGS

FIGS. 10A and 10B are diagrams illustrating examples of arrangement of an image pickup element with respect to a polarization separation element in the endoscope observation system according to the present invention, wherein FIG. 10A shows an example in which the image pickup element is located on a refection side, whereas a light absorber is located on a transmission side, and FIG. 10B shows an example in which the image pickup element is located on the transmission side, whereas the light absorber is located on the reflection side;

FIGS. 11A, 11B, and 11D are diagrams showing examples of the effective wavelength of the image pickup element with respect to the reflection characteristics of the polarization separation element in the endoscope observation system according to the present invention, wherein FIG. 11A shows an example in which the polarization separation element has the property of separating light into P-polarized light and S-polarized light on a long wavelength side and the effective wavelength of the image pickup element covers the wavelength bands of both the P-polarized light and S-polarized light resulting from the separation, FIG. 11B shows an example in which the polarization separation element has the property of separating light into the P-polarized light and the S-polarized light on a short wavelength side and the effective wavelength of the image pickup element covers the wavelength bands of both the P-polarized light and S-polarized light resulting from the separation, FIG. 11D shows an example in which the polarization separation element has the property of separating light into the P-polarized light and the S-polarized light on the long wavelength side and the effective wavelength of the image pickup element covers the wavelength band of one of the P-polarized light and S-polarized light resulting from the separation;

FIGS. 14A, 14B, and 14C are graphs showing the characteristics of wavelength bands and optical elements for light used in the endoscope observation system in Example 1, wherein FIG. 14A shows the transmission characteristics (two wavelength bands used as illumination light in a polarization observation mode) of two filters for the polarization observation mode which are provided in the light source section, and the transmission characteristics (the transmission wavelength bands of S-polarized light, P-polarized light, and non polarized light) of a polarization separation element provided in an illumination optical system, FIG. 14B shows two wavelength bands used as illumination light in the polarization observation mode and the transmission characteristics (the transmission wavelength bands of S-polarized light, P-polarized light, and non polarized light) of a polarization separation element provided in an image pickup optical system, and FIG. 14C shows the transmission characteristics (in this case, the wavelength bands of R (Red), G (Green), and B (Blue) used as illumination light in a non polarization observation mode) of a filter for the non polarization observation mode which is provided in the light source section, and the transmission characteristics (the wavelength bands of S-polarized light, P-polarized light, and non polarized light) of the polarization separation element provided in the illumination optical system;

FIGS. 16A, 16B, and 16C are graphs showing the characteristics of wavelength bands and optical elements for light used in an endoscope observation system in Example 2 of the present invention, wherein FIG. 16A shows the transmission characteristics (two wavelength bands used as illumination light in the polarization observation mode) of two filters for the polarization observation mode which are provided in a light source section, and the transmission characteristics (the transmission wavelength bands of S-polarized light, P-polarized light, and non polarized light) of a polarization separation element provided in an illumination optical system. FIG. 16B shows two wavelength bands used as illumination light in the polarization observation mode and the transmission characteristics (the transmission wavelength bands of S-polarized light, P-polarized light, and non polarized light) of a polarization separation element provided in an image pickup optical system, and FIG. 16C shows transmission characteristics (in this case, the wavelength bands of R (Red), G (Green), and B (Blue) used as illumination light in the non polarization observation mode) of a filter for the non polarization observation mode which is provided in the light source section, and the transmission characteristics (the wavelength bands of S-polarized light, P-polarized light, and non polarized light) of the polarization separation element provided in the illumination optical system;

FIGS. 17A and 17B are graphs showing the characteristics of wavelength bands and optical elements for light used in an endoscope observation system in Example 3 of the present invention, wherein FIG. 17A shows the transmission characteristics (two wavelength bands used as illumination light in the polarization observation mode) of two filters for the polarization observation mode which are provided in a light source section, and the transmission characteristics (the transmission wavelength bands of S-polarized light, P-polarized light, and non polarized light) of a polarization separation element provided in an illumination optical system, and FIG. 17B shows two wavelength bands used as illumination light in the polarization observation mode and the transmission characteristics (the transmission wavelength bands of S-polarized light, P-polarized light, and non polarized light) of a polarization separation element provided in an image pickup optical system;

FIGS. 18A and 18B are graphs showing the characteristics of wavelength bands and optical elements for light used in an endoscope observation system in Example 4 of the present invention, wherein FIG. 18A shows the transmission characteristics (three wavelength bands used as illumination light in the polarization observation mode) of three filters for the polarization observation mode which are provided in a light source section, and the transmission characteristics (the transmission wavelength bands of S-polarized light, P-polarized light, and non polarized light) of a polarization separation element provided in an illumination optical system, and FIG. 18B shows three wavelength bands used as illumination light in the polarization observation mode and the transmission characteristics (the transmission wavelength bands of S-polarized light, P-polarized light, and non polarized light) of a polarization separation element provided in an image pickup optical system;

FIGS. 20A, 20B, and 20C are graphs showing the characteristics of wavelength bands and optical elements for light used in an endoscope observation system in Example 5, wherein FIG. 20A shows the transmission characteristics (a wavelength band used as illumination light in the polarization observation mode) of a filter for the polarization observation mode which is provided in a light source section, and the transmission characteristics (the wavelength bands of S-polarized light, P-polarized light, and non polarized light) of a polarization separation element provided in an illumination optical system, FIG. 20B shows a wavelength band used as illumination light in the polarization observation mode and the transmission characteristics (the wavelength bands of S-polarized light and P-polarized light) of a polarization separation element provided in an image pickup optical system, and FIG. 20C shows the transmission characteristics of a mosaic filter on an image pickup element.

DETAILED DESCRIPTION OF THE PREFERRED EMBODIMENTS

First Embodiment

Figure 3:
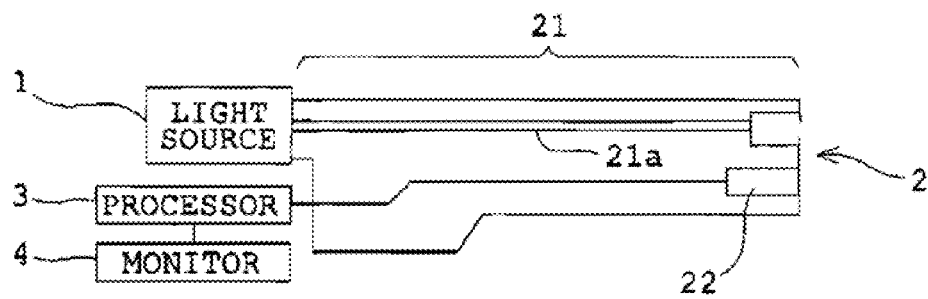
FIG. 3 is a schematic diagram showing the basic configuration of an endoscope observation system according to the present invention.
Figure 4A:
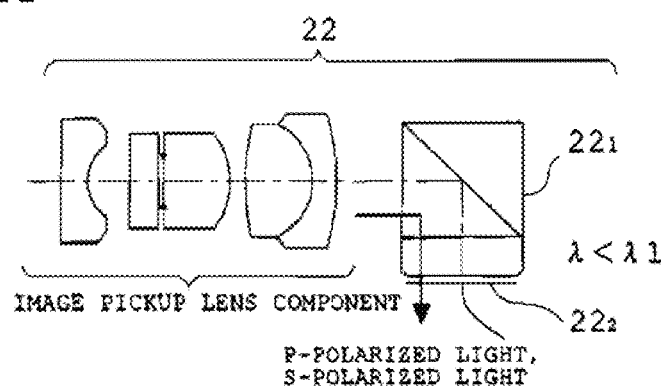
FIGS. 4A and 4B are diagrams showing an example off the configuration of an essential part of an endoscope observation system according to a first embodiment of the present invention.
Figure 4B:
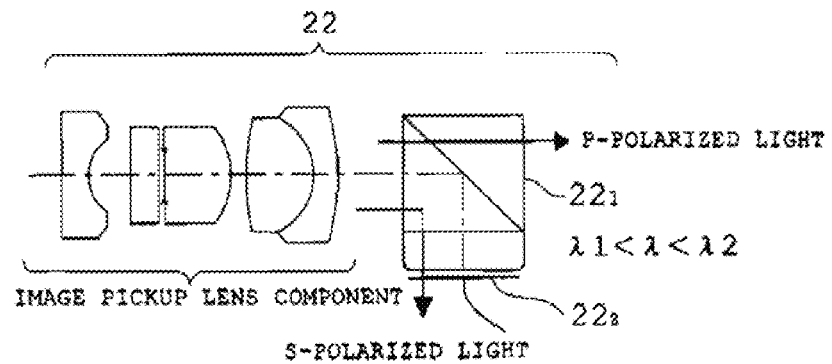
Figure 5:
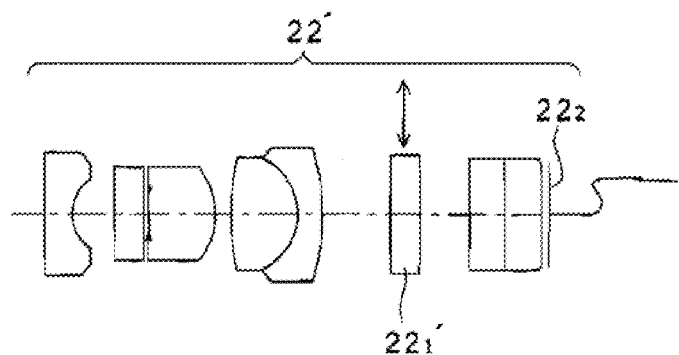
FIG. 5 is a diagram illustrating the configuration of a part of the conventional endoscope observation system which corresponds to the essential part in FIG. 4.

FIG. 3 is a schematic diagram illustrating the basic configuration of an endoscope observation system according to the present invention. FIGS. 4A and 4B are diagrams illustrating an example of the configuration of an essential part of an endoscope observation system according to a first embodiment of the present invention. FIG. 5 is a diagram illustrating the configuration of a part of a conventional endoscope observation system which corresponds to the essential part in FIGS. 4A and 4B, FIGS. 4A and 4B are graphs showing the reflection characteristics of a polarization element used in an image pickup optical system of the endoscope observation system according to the first embodiment. FIG. 5 is a diagram illustrating a variation of the basic configuration of an essential part of the endoscope observation system according to the first embodiment.

Figure 1:
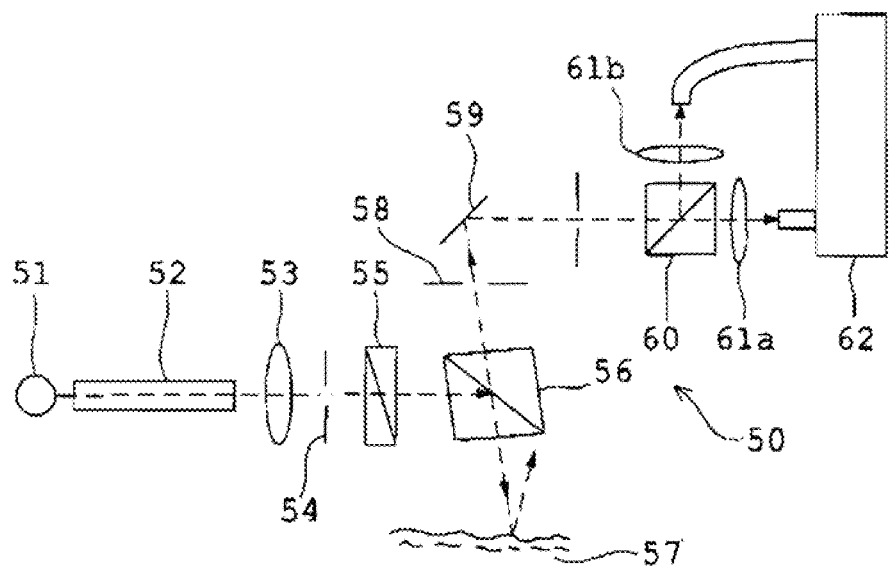
FIG. 1 is a diagram schematically illustrating the configuration of a conventional endoscope device for polarization observation.

As shown in FIG. 3, the endoscope observation system according to the first embodiment has a light source section 1, an endoscope 2 with an illumination optical system 21 and an image pickup optical system 22, an image processing device (processor) 3, and an image display device (monitor) 4. The light source section 1 is configured to generate illumination light with at least a part of a wavelength band varying between when a polarized light-based observation image is observed and when a non polarized light-based observation image is observed. The illumination optical system 21 has a light guide 21a and an irradiation side polarization separation element (not shown in FIG. 1). The irradiation side polarization separation element is provided in an irradiation side optical path (that is, in the optical path of the illumination optical system 21) through which an observation target is irradiated with illumination light from the light source section 1. The irradiation side polarization separation element is configured to subject the illumination light from the light source section 1 to polarization separation.

As shown in FIGS. 4A and 4B, the image pickup optical system 22 has a reception side polarization separation element $22_1$ and an image pickup element $22_2$. The reception side polarization separation element $22_1$ is configured such that in a particular wavelength band of light from the observation target, polarization separation is performed by transmitting only polarized light with a predetermined polarization component, while reflecting polarized light with a polarization component other than the predetermined polarization component, and all light in wavelength bands other than the particular wavelength band is transmitted or reflected. The image pickup element $22_2$ is positioned so as to receive the light transmitted or reflected (in the example shown in FIGS. 4A and 4B, reflected) by the reception side polarization separation element $22_1$.

Now, the reception side polarization separation element $22_1$ will be described in further detail. The reception side polarization separation element $22_1$ is composed of, for example, a prism type polarization (i.e., polarizing) beam splitter with a dichroic coating deposited thereon. The dichroic coating has the property of reflecting or transmitting (in FIG. 6 described below, reflecting) S-polarized light, P-polarized light, and non polarized light in the same manner in a wavelength band ($\lambda < \lambda_1$) shorter than a certain boundary wavelength $\lambda_1$. Furthermore, in a wavelength band ($\lambda_1 < \lambda < \lambda_2$) longer than the boundary wavelength $\lambda_1$ and shorter than a boundary wavelength $\lambda_2$, the dichroic coating exhibits the property of reflecting light with one of the polarization components (in this case, the S-polarized light for convenience), while transmitting light with the other polarization component (in this case, the P-polarized light for convenience). Thus, non polarization observation can be performed in the wavelength band shorter than the boundary wavelength $\lambda_1$. Polarization observation with the S-polarized light can be performed in the wavelength band longer than the boundary wavelength $\lambda_1$ and shorter than the boundary wavelength $\lambda_2$. The image processing device 3 uses images picked up by the image pickup element to execute predetermined image processing, for example, synthesis of the images or calculation of the difference between the images. As shown in FIGS. 4 and 4B, light enters the image pickup optical system 22 over the full effective diameter of the optical system irrespective of the type of illumination light with which the observation target is illuminated. Since the members of the image pickup optical system, including the reception side polarization separation element $22_1$ are fixed in the optical path, the polarized light-based observation image and the non-polarized light-based observation image, which are derived from the different types of illumination, are formed in the same region on the image pickup surface of the single image pickup element $22_2$. The image display device 4 is connected to the image processing device 3 to display the images processed by the image processing device 3.

The effects of the endoscope observation system according to the first embodiment configured as described above will, be described through a comparison with an image pickup optical system 22' configured such that a wavelength-independent polarization separation element $22_1'$ is removably installed in an optical path as shown in FIG. 5. To allow a polarized image in one direction to be observed, the image, pickup optical system needs to include polarization separation means in order to provide the polarized image. However, when an attempt is made to obtain a non polarized observation image via the same image pickup element with the polarization separation means left, in the optical path, one of the two types of polarized light is interrupted. Consequently, brightness is halved. Thus, to obtain the non polarized observation image with the brightness maintained via the same image pickup element, the wavelength-independent polarization separation element $22_1'$ may be configured to be removable from the optical path so as to be mechanically retracted from the optical path for non polarization observation, as is the case with the image pickup optical system 22' shown in FIG. 5. However, this increases the diameter of the image pickup optical system 22 and thus the diameter of the endoscope 2, as described above.

Furthermore, in the configuration in which the polarization separation element $22_1'$ is moved so as to be inserted into and removed from the optical path to switch between polarization observation-based image pickup and non polarization observation-based image pickup as shown in FIG. 5, simultaneously acquiring a polarized image and a non polarized image is difficult. However, in the endoscope observation system according to the first embodiment, as described above, the reception side polarization separation element $22_1$ performs polarization separation, in the particular wavelength band (in FIGS. 4A and 4B described below, the wavelength band longer than the boundary wavelength $\lambda 1$ and shorter than the boundary wavelength $\lambda 2$: $\lambda 1 < \lambda < \lambda 2$) of the light from the observation target, by transmitting the polarized light with one of the linear polarization components (in FIG. 6 described below, the P-polarized light), while reflecting the polarized light with the other linear polarization component (S-polarized light). In the wavelength band (in FIG. 6 described below, the wavelength band shorter than the boundary wavelength $\lambda 1$: $\lambda < \lambda 1$) other than the particular wavelength band, the reception side polarization separation element $22_1$ exhibits the same transmission and reflection characteristics for the polarized light and for the non polarized light. Thus, the non polarization observation can be performed in the wavelength band shorter than the boundary wavelength band $\lambda 1$. The polarization observation can be performed in the wavelength band longer than the boundary wavelength $\lambda 1$ and shorter than the boundary wavelength $\lambda 2$.

In the observation system described in Japanese Patent Laid-Open No. 2003-47588, since the reception side polarization separation element is left in the optical path, the polarized light in the wavelength band other than the particular wavelength band is cut during the non polarization observation. However, because of the above-described configuration, the endoscope system according to the first embodiment can use this polarized light for the non polarization observation with the reception side polarization separation element $22_1$ left in the optical path, while maintaining the brightness of normal light. This prevents the diameter of the image pickup optical system 22 from being increased, enabling a reduction in the diameter of the endoscope 2.

Figure 6:
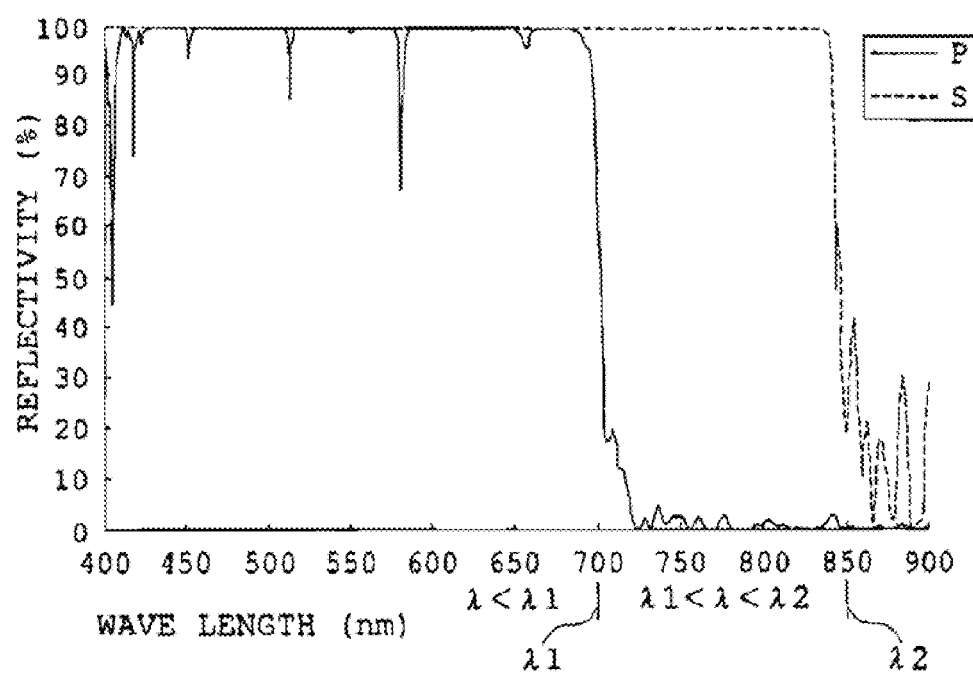
FIG. 6 is a graph showing reflection characteristics of a polarization element used in an image pickup optical system of the endoscope observation system according to the first embodiment.

FIG. 6 shows an example of the reflection characteristics of a prism type polarization beam splitter with a dichroic coat applied thereto, as the reception side polarization separation element $22_1$, which is applicable to the endoscope observation system according to the first embodiment, in view of the oblique incidence characteristic of the prism type beam splitter with the dichroic coat applied thereto, the distance between the boundary wavelengths $\lambda 1$ and $\lambda 2$, which determines the polarization observation wavelength band, is desirably at least 30 nm. When the distance between the boundary wavelengths $\lambda 1$ and $\lambda 2$ is 30 nm, a light source for polarization observation is preferably a light source such as an LD which involves a single wavelength and polarization.

In the example in FIG. 6, the boundary wavelength $\lambda 1$ is set in a wavelength band between 650 nm and 750 nm (in this case, $\lambda 1 = 700$ nm). The boundary wavelength $\lambda 2$ is set in a wavelength band between 800 nm and 1,000 nm (in this case, $\lambda 2=850$ nm). In this case, the non polarization observation wavelength band is a visible wavelength band. The polarization observation wavelength band is a near infrared wavelength band. This allows the non polarization observation in the visible wavelength band, that is, the normal light (white) observation, and the polarization observation (infrared wavelength band) to be simultaneously observed on the same axis without the need to provide the image pickup optical system 22 with a mechanical structure for switching the polarization separation element $22_1$. Furthermore, with this wavelength setting, the polarized light cut during the non polarization observation is light in the near infrared wavelength band. Thus, the brightness of the observation image in the visible wavelength band is not substantially affected.

Figure 7:
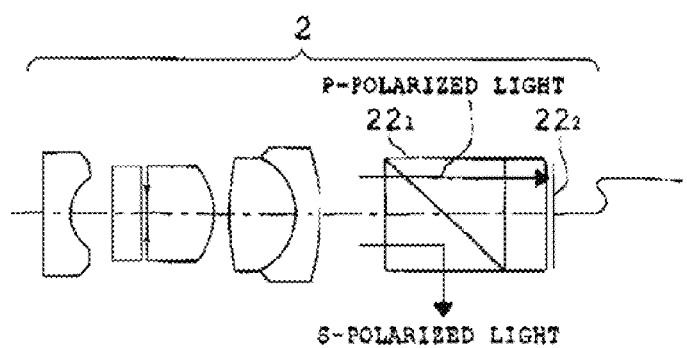
FIG. 7 is a diagram illustrating a variation of the basic configuration of the essential part of the endoscope observation system according to the first embodiment.

The boundary wavelength $\lambda 1$ may be set such that the polarization observation wavelength slightly overlaps the normal light (that is, the boundary wavelength $\lambda 1$ is set to about 650 nm, which belongs to the visible wavelength band) unless the brightness of the non polarization observation is affected. Furthermore, in the endoscope observation system according to the first embodiment, the image pickup element $22_2$ may be located so as to allow observation of light transmitted through the prism type polarization beam splitter $22_1$ with the dichroic coat applied thereto as shown in FIG. 7, in this case, the polarization separation element $22_1$ need not necessarily reflect most of the S-polarized light in a wavelength band between boundary wavelengths $\lambda 1'$ and $\lambda 2'$. Instead, part or moat of the B-polarized light may be absorbed. By absorbing the polarized light, unwanted polarized light can be prevented from entering the image pickup element $22_2$.

In the example in FIG. 7, the polarization observation of the P-polarized light can be performed in the wavelength band longer than the boundary wavelength $\lambda 1'$ and shorter than the boundary wavelength $\lambda 2'$. The non polarization observation can be performed in a wavelength band longer than the boundary wavelength $\lambda 2'$. For example, setting the boundary wavelength $\lambda 2'$ between 350 nm and 400 nm allows the non polarization observation in the visible wavelength band and the polarization observation in an ultraviolet to blue wavelength band to be simultaneously performed on the same axis.

As described above, the endoscope observation system according to the first embodiment includes the wavelength-dependent polarization beam splitter as the reception side polarization separation element. The endoscope observation system thus enables an increase in the diameter of the image pickup optical system to be prevented without the need for a mechanical structure for switching the polarization member. The endoscope observation system also allows the observation based on the non polarized light such as the normal light and the polarized light-based observation to be substantially simultaneously performed using the same image pickup element, while minimizing a decrease in the quantity of light for the non polarized light-based observation. In the endoscope observation system according to the first embodiment, like the reception side polarization separation element, the irradiation side polarization separation element preferably performs polarization separation, in the particular wavelength band of the illumination light from the light source section, by transmitting the polarized light with the predetermined polarization component while reflecting the polarized light with the polarization component other than the predetermined polarization component, and in the wavelength band other than the particular wavelength band, exhibits the same transmission and reflection characteristics for both the polarized light and the non polarized light.

Thus, the brightness of irradiation light in the observation modes other than the polarization observation is substantially similar to that of illumination light from an illumination optical system without a polarizer. This prevents the observation modes other than the polarization observation mode from being affected by polarization. The endoscope observation system thus enables an increase in the diameter of the illumination optical system to be prevented without the need for a mechanical structure for switching the polarization member. The endoscope observation system also allows the illumination light to be provided in the non polarization observation mode and the polarization observation mode using the same illumination optical system while minimizing a decrease in the quantity of observation light for the observation based on the non polarized light such as the normal light.

Furthermore, in the endoscope observation system according to the first embodiment, preferably, in the polarization separation wavelength band, each of the irradiation side polarization separation element and the reception side polarization separation element separates light into two orthogonal rays of linearly polarized light. In general, many elements other than polarizing plates such as phase plates are required to separate light into polarized light other than the linear polarization component such as circularly polarized light. By separating light into two types of polarized light with orthogonal linear polarization components such as the P-polarized light and the S-polarized light, the configuration of the polarization element can be simplified. Additionally, the linearly polarized light is suitable for observing a directional microstructure such as fiber.

Furthermore, in the endoscope observation system according to the first embodiment, preferably, each of the irradiation side polarization separation element and the reception side polarization separation element is of the prism type. The prism type polarization separation element is made up of common optical glass and a dichroic coat thin film formed toy deposition or ion sputtering. The dichroic coat thin film is sandwichingly held by the prism. This configuration facilitates the polarization separation. That is, the configuration stabilizes mechanical and optical characteristics compared to wire grid polarizers the characteristics of which are likely to be varied by pressure and crystal-containing polarizers the crystal performance of which is affected by birefringence. Additionally, the prism type facilitates incorporation of the elements into the device and adjustment following the incorporation.

Furthermore, in the endoscope observation system according to the first embodiment, preferably, the irradiation side polarization separation element and the reception side polarization separation element are arranged such that in the polarization separation wavelength band, a polarization direction of the polarization component transmitted by the irradiation side polarization separation element is orthogonal to a polarization direction of the polarization component transmitted by the reception side polarization separation element. This allows the image pickup optical system to cut the same polarization component as that of the illumination light to pick up an image of the polarization component perpendicular to the polarization component of the illumination light. Thus, information on light scattering in the living body can be obtained.

This will be described in detail. For example, the illumination light side polarization component is assumed to the S-polarized light. The polarization condition of light reflected by a cortical layer of the living body remains unchanged. On the other hand, the polarization condition of light scattering in a deep layer of the living body is disturbed. As a result, the light has not only the polarization component of the S-polarized light but also the polarization component of the P-polarized light, having a polarization direction orthogonal to that of the S-polarized light. Thus, the irradiation side polarization separation element and the reception side polarization separation element are arranged such that in the polarization separation wavelength band, the polarization direction of the polarization component (S-polarized light) transmitted by the irradiation side polarization separation element is orthogonal to the polarization direction of the polarization component (S-polarized light) transmitted by the reception side polarization separation element. Then, the S-polarized light with the same polarization component as that of the illumination light is cut on the image pickup optical system side. Only the P-polarized light is transmitted and an image of the light is picked up. At this time, the P-polarized light is part of the light scattering in the deep layer of the living body, which contains the S-polarized light. However, in the scattering light, the P-polarized light and the S-polarized light are expected to have a substantially equal light intensity. Thus, the intensity of the scattering light is obtained by doubling the intensity of the P-polarized light subjected to image pickup by the image pickup element.

Furthermore, in the endoscope observation system according to the first embodiment, preferably, each of the irradiation side polarization separation element and the reception side polarization separation element has a boundary wavelength which is longer than 580 nm between a transmission wavelength band and the polarization separation wavelength band. This enables red to infrared polarization observation without seriously affecting the wavelength band (400 to 650 nm) of the visible light used for the non polarization observation. When the boundary wavelength $\lambda 1$ is set to 580 to 650 nm, the brightness of red decreases. However, the color tone can be appropriately adjusted for observation by color balancing or a color correction filter. Additionally, a wavelength longer than 580 nm is not substantially affected by biological light absorption. Thus with this wavelength, information on scattering of the polarized light has only to be considered.

Second Embodiment

Figure 2:
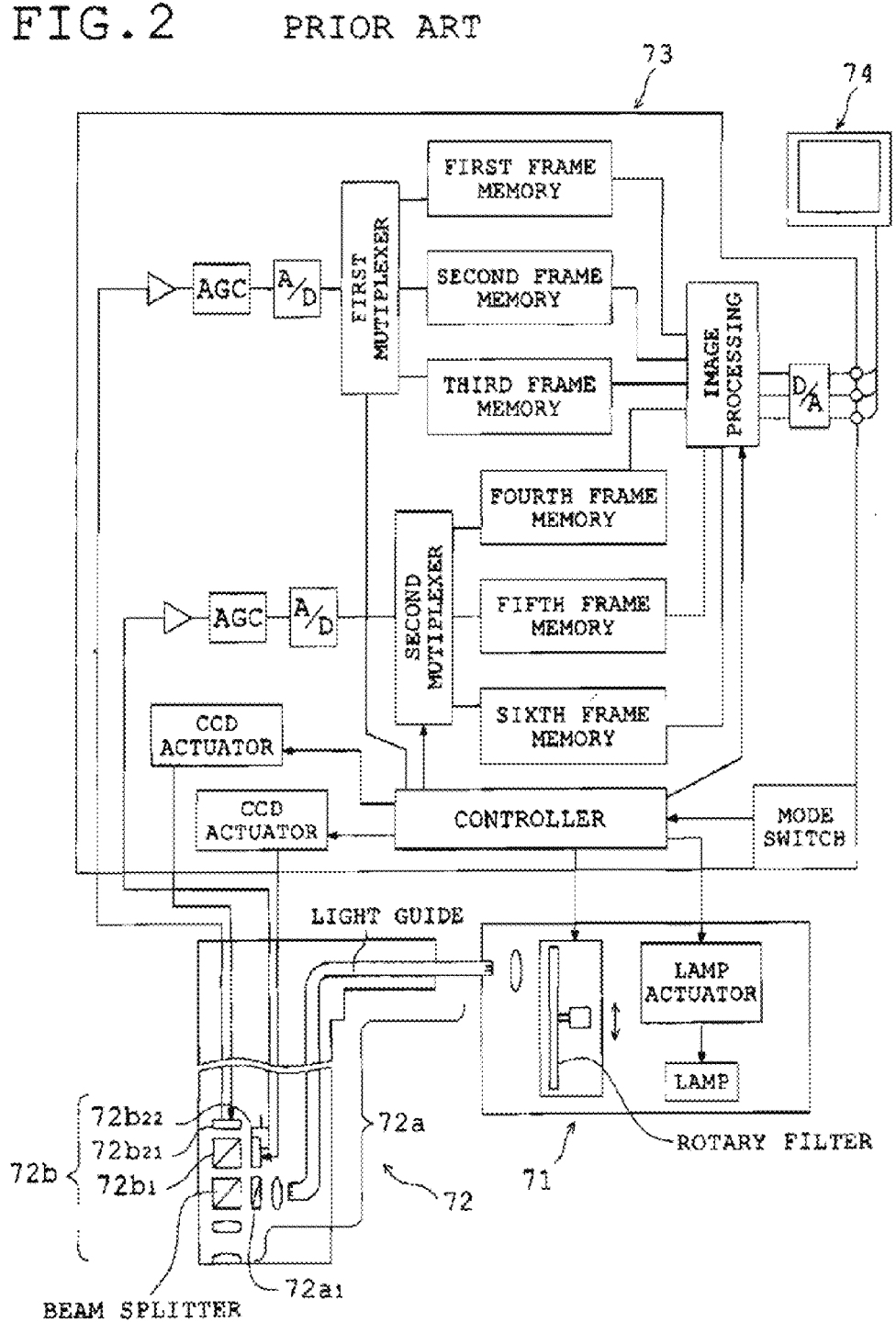
FIG. 2 is a diagram schematically illustrating the configuration of an endoscope observation system described in Japanese Patent Laid-Open No. 2003-47588.
Figure 8:
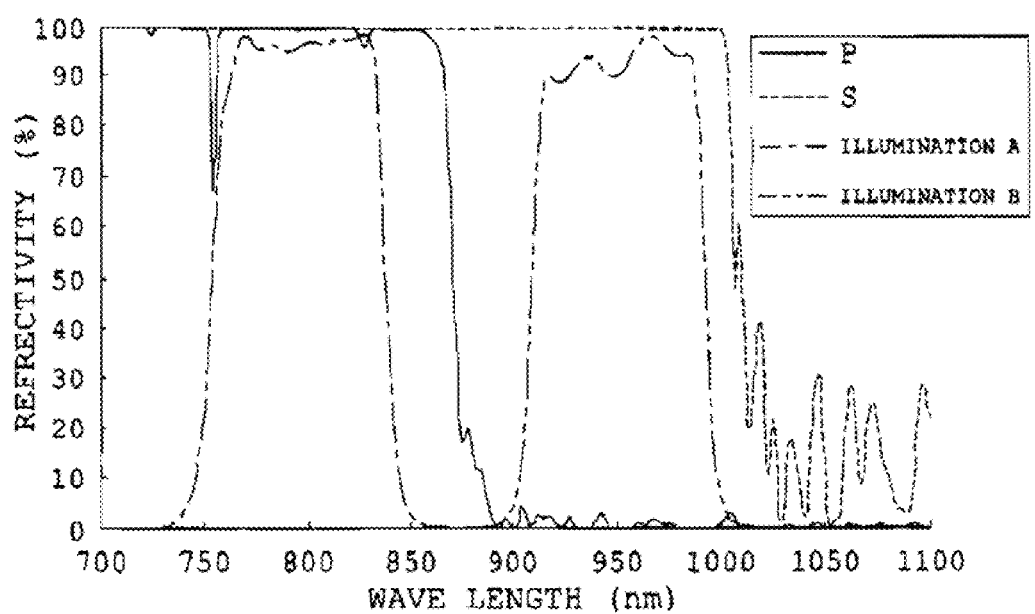
FIG. 8 is a graph showing reflection characteristics of a polarization element used in an illumination optical system and a polarization element used in an image pickup optical system, in an endoscope observation system according to a second embodiment of the present invention.
Figure 9:
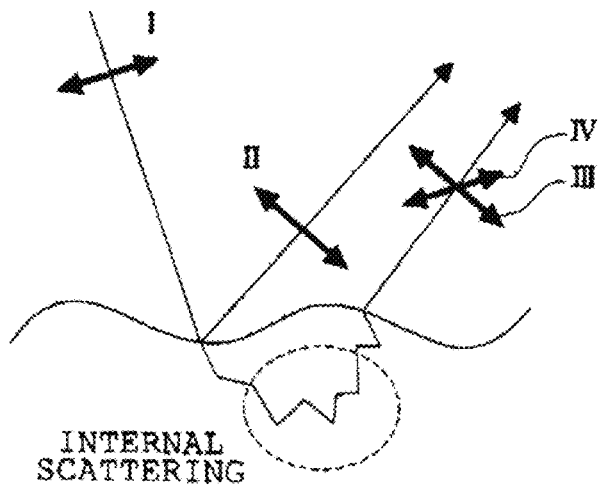
FIG. 9 is a diagram illustrating a principle based on which a difference image is obtained.

FIG. 8 is a graph showing the reflection characteristics of polarization elements used in an illumination optical system and an image pickup optical system, respectively, in an endoscope observation system according to a second embodiment of the present invention. FIG. 9 is a diagram illustrating a principle based on which a difference image is obtained. The basic configuration of the endoscope observation system according to the second embodiment and the basic configuration of the optical members of the image pickup optical system are substantially the same as those in the endoscope observation system according to the first embodiment shown in FIGS. 3, 2A, and 2B.

The endoscope observation system according to the second embodiment has the configuration of the first embodiment and is further configured such that a light source section 1 emits two types of light in different wavelength bands as the illumination light in the polarization observation mode (this configuration is not shown in the drawings). An image processing device (processor) 3 is configured to calculate image information obtained by allowing the image pickup element to pick up an image of the light in one of the two different wavelength bands and image information obtained by allowing the image pickup element to pick up an image of the light in the other wavelength band, to synthesize the information into one image. The image processing device 3 is connected to an image display device 4 so that the processed image is displayed on the image display device 4.

The effects of the endoscope observation system according to the second embodiment configured as described above will be described through a comparison with an image pickup optical system 22' configured such that a wavelength-independent polarization separation element $22_1$' is removably installed in the optical path as shown in FIG. 5. When a mirror is irradiated with light with a polarization component of a certain polarization direction, reflected and returned light has the same polarization direction as that of the irradiation light. On the other hand, if a scatterer is irradiated with light with a polarization component of a certain polarization direction, multiple scattering occurs in the scatterer to disturb the polarization condition. Thus, the polarization direction of the returning light is not necessarily the same as that of the irradiation light.

The endoscope observation system according to the second embodiment uses this principle to allow the scattering condition of the mucosa or the like to be observed in images by observing changes in the polarization condition of light returning from the mucosa, in addition to exerting the effects of the configuration of the first embodiment. For example, when the scattering condition of the mucosa is observed using polarization, it is necessary to determine the difference between an image (non polarized image) of polarized light returning from the mucosa and an image (polarized image) obtained by extracting only a polarization component with certain characteristics from the non polarized image, to analyze how the light and polarization are changed.

To allow the difference between the polarized and non polarized images in the same wavelength band to be determined, the wavelength-independent polarization separation element 22' is removably constructed in the optical path in an image pickup optical system 22 as shown in FIG. 5. Then, to allow the non polarization observation to be performed via the same image pickup element, the polarization separation element $22_1$' is mechanically retracted from the optical path. However, this increases the diameter of the image pickup optical system 22 and thus the diameter of an endoscope 2. Furthermore, a relatively long switching time is required to mechanically install and remove the polarization separation element $22_1$' in and from the optical path. If a subject is shifted during the installation or removal, the difference may not be accurately determined.

On the other hand, provided that the wavelength-dependent polarization separation element $22_1$ is used to obtain the polarized and non polarized images in different wavelength bands as in the case of the configuration according to the first embodiment, the endoscope observation system allows the observation based on the non polarized light such as the normal light and the polarization observation to be performed using the same image pickup element without the need to switch the polarization separation element $22_1$, while minimizing a decrease in the quantity of light for the non polarized light-based observation. Furthermore, since the non polarized image and the polarized image can be simultaneously acquired, the deviation between the images can be reduced. However, in general, substances exhibit different absorption and reflection characteristics depending on the wavelength. Thus, calculating the difference in polarization by this technique is expected to be difficult.

However, given the application is limited to the endoscope, the reflection spectrum of the observation target such as the mucosa obtained via the endoscope is substantially constant between 750 nm and 1,000 nm. This can be estimated from the fact that when the interior of the body is observed by infrared imaging (IRI) using two wavelength bands, a wavelength band of 750 nm to 840 nm and a wavelength band of 910 to 990 nm, colors are prevented from varying between the respective resulting images except for overheated blood and ICG (Indocyanine Green), and white balancing makes the entire images appear white (this means that the wavelength bands have the same wavelength balance).

Thus, the endoscope observation system according to the second embodiment uses the basic configuration of the endoscope observation system according to the first embodiment and further uses two types of light in respective wavelengths (bands) within a wavelength band of 750 to 1,000 nm. The endoscope observation system according to the second embodiment limits the polarization of the light of one of the wavelengths (bands), while avoiding limiting the polarization of the light of the other wavelength (band). Then, the difference between the images based on the respective wavelength bands can be determined to be the difference between the polarized and non polarized images. In this case, the effect of the polarization is dominant on the difference.

This will be described in further detail with reference to the drawings. By way of example, it is assumed that the wavelength bands of the IRI are used without change, in the configuration shown in FIG. 3, the light source section 1 is configured such that light emitted by a light source (not shown in the drawings) is consecutively switched between illumination light A in a wavelength band mesial magnitude of 750 to 840 nm and illumination light B in a wavelength band mesial magnitude of 910 to 990 nm in a time-division manner via a rotary filter made up of a filter located on a turret or the like (this arrangement is not shown in detail for convenience). The illumination light A and the illumination light B pass through a light guide 21a and sequentially enter the irradiation side polarization separation element (not shown in the drawings) by being sequentially switched in a time-division manner. The irradiation side polarization separation element (not shown in the drawings) transmits and emits light with a particular polarization component (in this case, the P-polarized light) to the observation target.

The image pickup optical system 22 includes a reception side polarization separation element $22_1$. The reception side polarization separation element $22_1$ is composed of a prism type polarization beam splitter with a dichroic coat applied thereto. The reception side polarization separation element $22_1$ has the optical property of reflecting both the P-polarized light and S-polarized light (and the non polarized light) in a wavelength band shorter than 870 nm, and between 870 nm and 1,000 nm, reflecting and guiding only the S-polarized light to an image pickup element $22_2$. Images of the illumination light A and the illumination light B are picked up via the image pickup element $22_2$ in a time-division manner by means of surface-sequential illumination as described above. Alternatively, the light source section 1 may simultaneously emit the illumination light A and the illumination light B. Furthermore, a mosaic filter may be provided on the image pickup element $22_3$ so that different pixels are assigned to the respective channels for image pickup.

Here, the image obtained by the image pickup element $22_2$ by irradiating the observation target with the illumination light A corresponds to all of the light (that is, the non polarized light) returning from the observation target. The image obtained by the image pickup element $22_2$ by irradiating the observation target with the illumination light B corresponds to a part of the light returning from the observation target which travels in a particular polarization direction. Certain colors may be assigned to the image based on the illumination light A, whereas colors different from the certain colors may be assigned to the image based on the illumination light B. Then, the polarization difference can be expressed based on how the colors are mixed together. Alternatively, an image processing device (processor) 3 may internally calculate the pixels of the illumination light A and the corresponding pixels of the illumination light B to obtain one color channel, which may then be superimposed on a simultaneously picked-up image of visible light of at most 700 nm. A difference image is thus created to allow the reflected light, for example, only from the cortical layer to be obtained.

The principle based on which the difference image is obtained will be described with reference to FIG. 9. For example, when the living body is irradiated with illumination light only with a polarization component I in a given direction (in this case, the P-polarized light or horizontally polarized light), the polarization condition of light reflected by the cortical layer of the living body remains unchanged. The light thus has a polarization component II that is the same as a polarization component I. On the other hand, the polarization condition of light entering a deep layer is disturbed when the light returns after being scattered. As a result, the light has a polarization component III that is the same as the polarization component I and a polarization component IV (in this case, the S-polarized light or perpendicularly polarized light) of a polarization direction orthogonal to that of the polarization component I. Here, the endoscope observation system according to the second embodiment provides a non polarized image of light containing all of the polarization components II, III, and IV (the P-polarized light and S-polarized light in one of the wavelength bands (for example, the wavelength band of the illumination light A)). The endoscope observation system according to the second embodiment also provides a polarized image of light with the polarization component IV (the S-polarized light in the other wavelength band (for example, the wavelength band of the illumination light B)). A comparison of the images in the respective bands allows information on scattering in the living body or the like to be obtained.

Furthermore, according to the endoscope observation system according to the second embodiment, the image processing device 3 can use the non polarized image and polarized image obtained as described above to execute the calculation shown below. Light scattered by the deep layer has random polarization components. Thus, light with the polarization component III (P-polarized light) and light with the polarization component IV (S-polarized light) are expected to have a substantially equal strength (the intensity of the polarization component III≈the intensity of the polarization component IV). Accordingly, the image of reflected light from the cortical layer can be exclusively calculated.

(non polarized image) −

(polarized image of illumination light in the other wavelength band) ×

2 = (polarization component II + polarization component III + polarization component IV) − polarization component IV × 2 = polarization component II

Therefore, the endoscope observation system according to the second embodiment provides the image only of the cortical layer of the living body.

Thus, according to the endoscope observation system according to the second embodiment, the illumination light in the polarization observation mode is made up of light in the two different wavelength bands.

Consequently, information on scattering in the living body can be obtained as follows. The observation target is irradiated with polarized illumination light in two different wavelength bands. The image pickup optical system picks up an image of the irradiation light in one of the wavelength bands reflected by the observation target without change (light with the polarization condition unchanged and light with the polarization condition disturbed). The image pickup optical system separates the irradiation light in the other wavelength band into the light with the polarization condition unchanged and the light with the polarization condition disturbed. The image pickup optical system then picks up an image of the light with the polarization condition disturbed. Then, images obtained from the illumination light in the respective wavelength bands are compared with each other. Furthermore, calculation of the images provides a polarization difference image and information on the cortical layer of the living body.

The endoscope observation system according to the second embodiment preferably includes the image processing device that calculates image information obtained by allowing the image pickup element to pick up an image of the light in one of the two different wavelength bands and image information obtained by allowing the image pickup element to pick up an image of the light in the other wavelength band, to synthesize the image information into one image.

Information on scattering in the living body can be provided in an easy-to-understand manner by performing imaging using the image processing device that calculates and synthesizes the images in the respective wavelength bands. Furthermore, the endoscope observation system according to the second embodiment may superimpose the result of the above-described calculation on an image obtained by irradiation with the illumination light in the observation mode other than the polarization observation mode, such as the normal light, to synthesize the result and the image into one image. A small image area in which an image in the polarization observation mode is displayed may be provided beside an image display in an observation mode other than the polarization observation mode, such as an image of the normal light, mainly used for endoscope observations. Alternatively, a button may be installed at any position in the endoscope observation system so that the observation mode to be displayed can be switched by depressing the button, allowing the images to be compared with each other.

Additionally, the endoscope observation system according to the second embodiment is preferably configured such that the wavelength of illumination light in the polarization observation mode is longer than 580 nm. Only a small (Quantity of the illumination light with a wavelength which is longer than 580 nm is absorbed by the living body. Thus, the calculation result is prevented from being affected by the absorption. Consequently, information on the scattering in the living body can be provided. The other effects of the endoscope observation system according to the second embodiment are almost the same as those of the endoscope observation system according to the first embodiment.

Figure 10A:
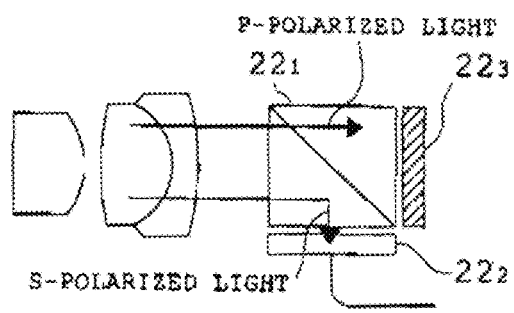
Figure 10B:
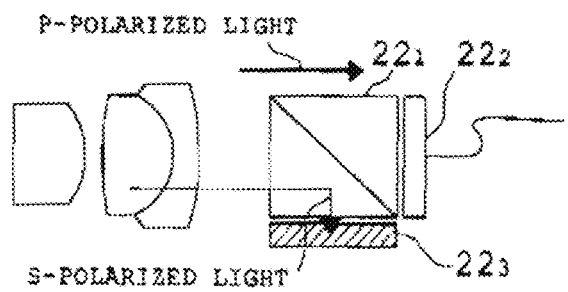

The location of the image pickup element $22_2$ with respect to the polarization separation element $22_1$ is such that the image pickup element $22_2$ may be located on either the S-polarized light side or the P-polarized light side, as shown in FIGS. 4A, 4B, and 7 and further in FIGS. 10A and 10B; the S-polarized light and the P-polarized light are obtained by separating the illumination light, in this case, a light absorber $22_1$ is preferably provided on the other side on which the image pickup element $22_2$ is not provided. In this case, possible stray light can be prevented, inhibiting unwanted light from entering the image pickup element. This correspondingly improves the accuracy and image quality of picked-up images.

Figure 11A:
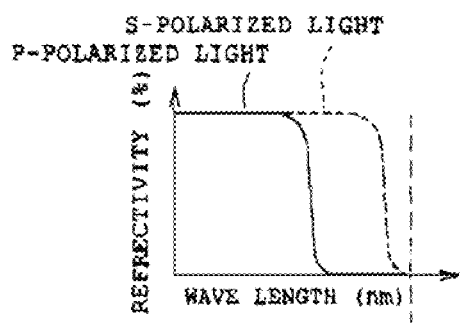
Figure 11B:
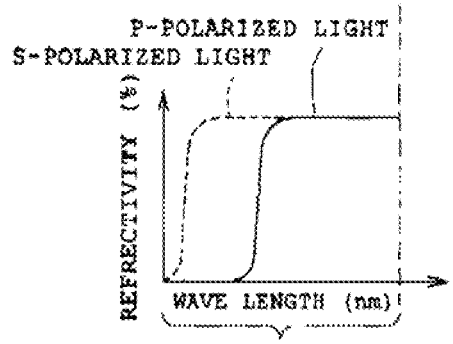
Figure 11C:
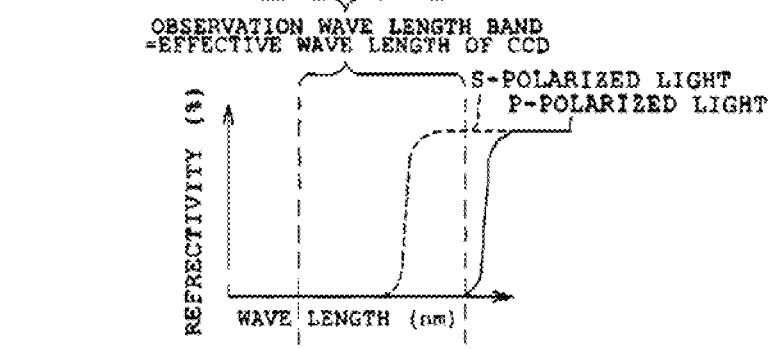
FIG. 11C shows an example in which the polarization separation element has the property of separating light into the P-polarized light and the S-polarized light on the short wavelength side and the effective wavelength of the image pickup element covers the wavelength band of one of the P-polarized light and S-polarized light resulting from the separation.
Figure 11D:
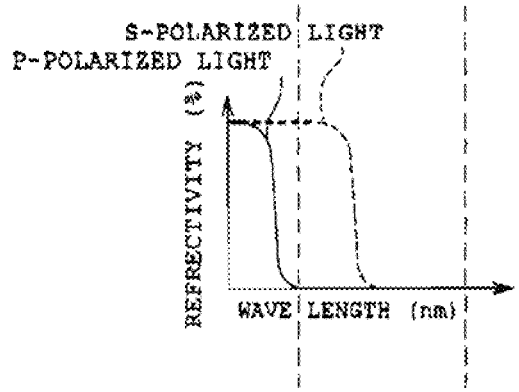

In the above-described embodiments, only one image pickup element is provided. However, the image pickup element may be provided on both optical paths into which the illumination light is separated by the polarization beam splitter which is a polarization separation element, so as to acquire both images resulting from the separation. This is also effective for enabling an increase in the diameter of the image pickup optical system to be prevented without the need for a mechanical structure for switching the polarization member, and allowing the observation based on the non polarized light such as the normal light and the polarization observation to be performed using the same image pickup element, while minimizing a decrease in the quantity of light for the non polarized light-based observation. Furthermore, the effective wavelength of the image pickup element may cover the wavelength bands of both the S-polarized light and P-polarized light into which the illumination light is separated by the polarization separation element, as shown in FIGS. 11A and 11B or the wavelength band of one of the S-polarized light and P-polarized light (in FIGS. 11C and 11D, the S-polarized light) into which the illumination light is separated by the polarization separation element, as shown in FIGS. 11C and 11D.

Now, examples of the endoscope observation system according to the present invention will be described with reference to the drawings.

Example 1

Figure 12:
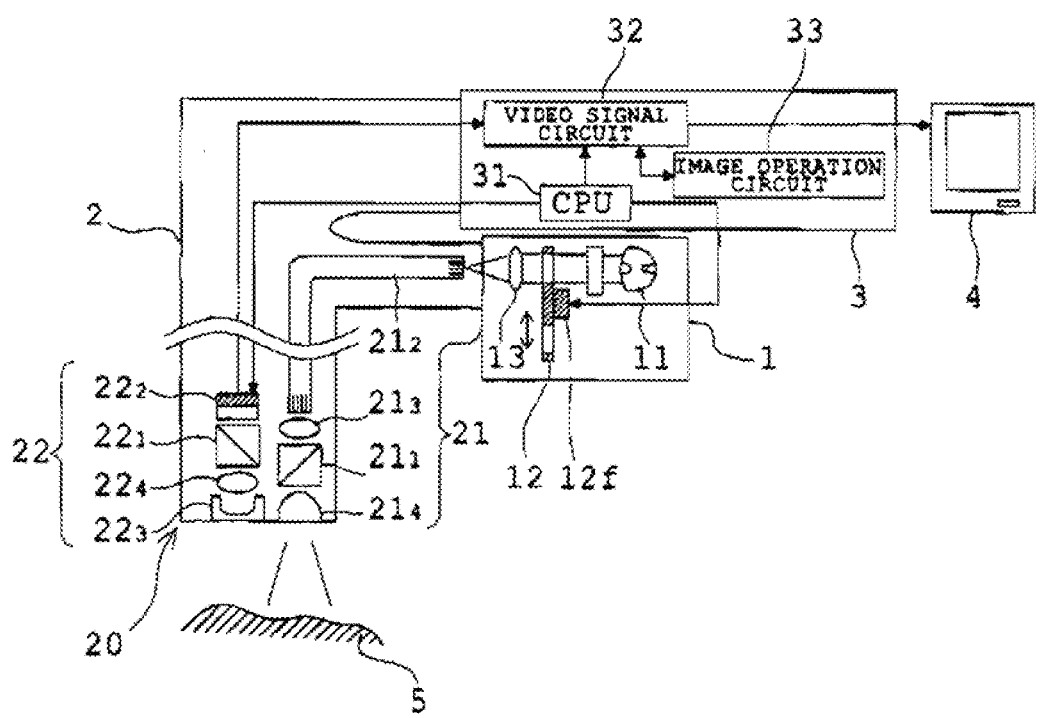
FIG. 12 is a schematic diagram showing the general configuration of an endoscope observation system in Example 1 of the present invention.
Figure 13:
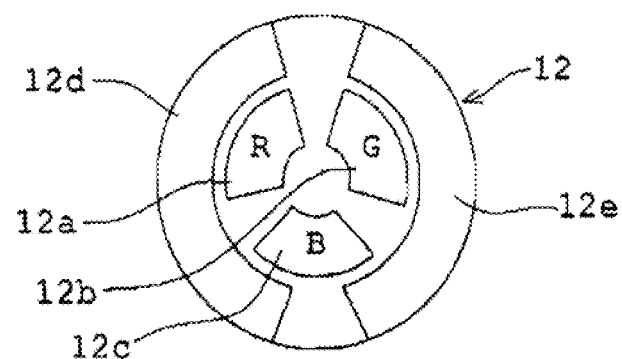
FIG. 13 is a diagram illustrating an example of the configuration of a rotary filter provided in a light source section of the endoscope observation system in FIG. 12.
Figure 14A:
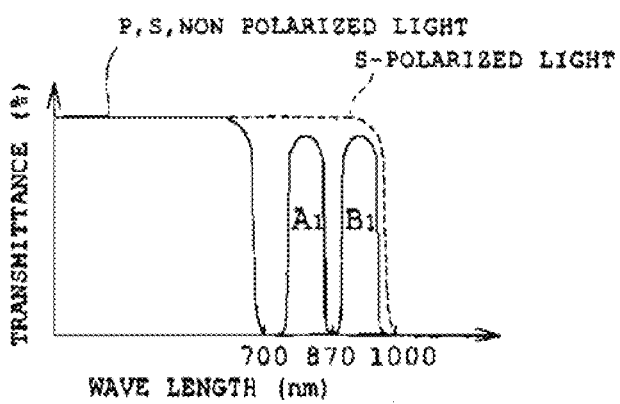
Figure 14B:
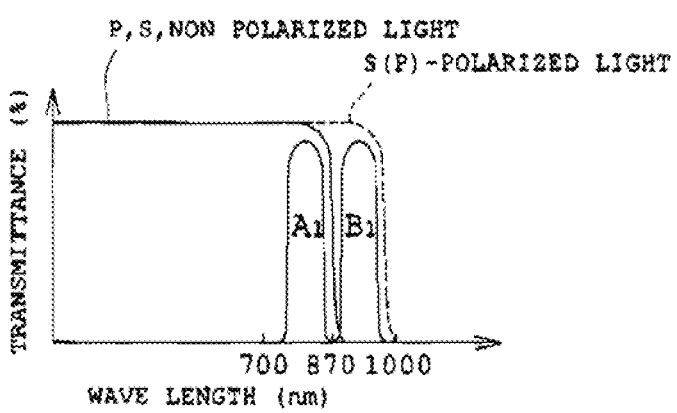
Figure 14C:
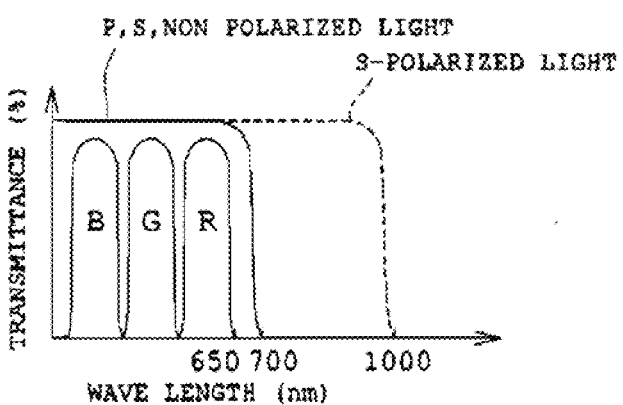
Figure 15:
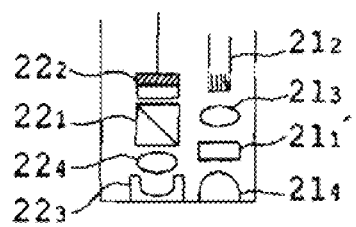
FIG. 15 is a partial diagram showing a variation of the illumination optical system in the endoscope observation device shown in FIG. 12.

FIG. 12 is a schematic diagram generally snowing the configuration of an endoscope observation system in Example 1 of the present invention. FIG. 13 is a diagram illustrating an example of the configuration of a rotary filter provided in a light source section of the endoscope observation system in FIG. 12. FIGS. 14A, 14B, and 14C are graphs showing the characteristics of wavelength bands and optical elements for light used in the endoscope observation system in Example 1. FIG. 14A shows the transmission characteristics (two wavelength bands used as illumination light in the polarization observation mode) of two filters for the polarization observation mode which are provided in the light source section, and the transmission characteristics (the transmission wavelength bands of S-polarized light, P-polarized light, and non polarized light) of a polarization separation element provided in an illumination optical system. FIG. 14B shows two wavelength bands used as illumination light in the polarization observation mode and the transmission characteristics (the transmission wavelength bands of S-polarized light, P-polarized light, and non polarized light) of a polarization separation element provided in an image pickup optical system. FIG. 14C shows the transmission characteristics (in this case, the wavelength bands of R (Red), G (Green), and B (Blue) used as illumination light in the non polarization observation mode) of a filter for the non polarization observation mode which is provided in the light source section, and the transmission characteristics (the wavelength bands of S-polarized light, P-polarized light, and non polarized light) of the polarization separation element provided in the illumination optical system. FIG. 15 is a partial diagram showing a variation of the illumination optical system in the endoscope observation device shown in FIG. 12.

The endoscope observation system in Example 1 has a light source section 1, an endoscope 2, an image processing device (processor) 3, and an image display device (monitor) 4. The light source section 1 has a light source 11, for example, a xenon lamp, which emits white light, and a rotary filter 12 made up of a filter group located on a turret. In FIG. 12, reference numeral 13 denotes a condensing lens that allows illumination light to enter an entry facet of a light guide $21_2$ described below.

As shown in FIG. 13, the rotary filter 12 is made up of a non polarization observation filter and a polarization observation filter arranged on the inner periphery side and outer periphery side, respectively of the turret. That is, an R filter 12a, a G filter 12b, and a B filter 12c as non polarization observation filters are arranged on the inner periphery side so that the rotary filter 12 is divided into the three pieces in a circumferential direction; as shown in FIG. 14C, the R filter 12a, the G filter 12b, and the B filter 12c have the properties of transmitting light in the wavelength bands of R (Red), G (Green), and B (Blue), respectively. Filters 12d and 12e as polarization observation filters are provided on the outer periphery side so that the rotary filter 12 is divided into the two pieces; as shown in FIG. 14A, the filter 12d has the property of transmitting only light in a predetermined wavelength band $A_1$ longer than 700 nm and shorter than 870 nm, and the filter 12e has the property of transmitting only light in a predetermined wavelength band $B_1$ longer than 870 nm and shorter than 1,000 nm. The light guide $21_2$ described below has the property of easily absorbing the light of B. Thus, a color correction filter is added to each of the R filter 12a and the G filter 12b to adjust output light quantity such that the light of R, the light of G, and the light of B are emitted from the light guide $21_2$ at the same rate.

Furthermore, the rotary filter 12 can be moved perpendicularly to the optical axis via a movement stage (not shown in the drawings) to allow the inner peripheral filters and the outer peripheral filters on the illumination optical path. The movement stage (not shown in the drawings) is controlled by a control section 31 provided in the processor 3 described below so that in the non polarization observation mode, the inner peripheral filters (non polarization observation filters) are arranged on the illumination optical path, whereas in the polarization observation mode, the outer peripheral filters (polarization observation filters) are arranged on the illumination optical path. The rotary filter 12 is rotationally driven via a motor 12f.

The endoscope 2 has an illumination optical system 21 and an image pickup optical system 22. The illumination optical system 21 and the image pickup optical system 22 are provided inside an elongate insertion section 20 that can be inserted into the celom.

The illumination optical system 21 has the light guide $21_2$, a lens $21_3$, an irradiation side polarization separation element $21_1$, and an illumination lens $21_4$. The light guide $21_2$ is a light guidance member through which the illumination light from the light source section 1 is transmitted (guided). The light guide $21_2$ is composed of fibers. The irradiation side polarization separation element $21_1$ is composed of a prism type polarization beam splitter with a dichroic coat applied thereto. As shown in FIG. 14A, the irradiation side polarization separation element $21_1$ has the property of processing the illumination light from the light source section 1 by transmitting all of the P-polarized light, the S-polarized light, and the non polarized light for light in a predetermined wavelength band which is shorter than 700 nm and which contains the wavelength bands of R, G, and B, while transmitting only the S-polarized light for light in a predetermined wavelength band which is longer than 700 nm and shorter than 1,000 nm and which contains the above-described predetermined wavelength bands $A_1$ and $B_1$. When used for observation not substantially affected by the polarization of the illumination light in the non polarization observation mode, the irradiation side polarization separation element $21_1$ may be composed of a flat plate-like polarizer $21_1'$ instead of the prism type as shown in FIG. 15.

The image pickup optical system 22 has an objective lens $22_3$, an image forming lens $22_4$, a reception side polarization separation element $22_1$, and an image pickup element $22_2$. The reception side polarization separation element $22_1$ is composed of a prism type polarization beam splitter with a dichroic coat applied thereto. As shown in FIG. 14B, the reception side polarization separation element $22_1$ has the property of transmitting all of the P-polarized light, the S-polarized light, and the non polarized light for light in a predetermined wavelength band which is shorter than 870 nm and which contains the wavelength bands of R, G, and B, while transmitting only the S-polarized light for light in a predetermined wavelength band which is longer than 870 nm and shorter than 1,000 nm and which contains the above-described predetermined wavelength band $B_1$.

Furthermore, the reception side polarization separation element $22_1$ is located so as to rotate the transmitted light through 90 degrees so that the polarization direction of the polarization component (S-polarized light) transmitted in the polarization separation wavelength band (that is, the predetermined wavelength band which is longer than 870 nm and shorter than 1,000 nm and which contains the above-described predetermined wavelength band $B_1$) is orthogonal to the polarization direction of the polarization component (S-polarized light) transmitted in the polarization separation wavelength band of the irradiation side polarization separation element $21_1$ (that is, the predetermined wavelength band which is longer than 700 nm and shorter than 1,000 nm and which contains the above-described predetermined wavelength bands $A_1$ and $B_1$) (in FIG. 12, for convenience, the boundary between the P-polarized light and S-polarized light into which the reception side polarization separation element $22_1$ separates the incident light is shown by a diagonal line, but the boundary line is actually located in an orientation in which the boundary line is not seen on the sheet of the drawing). Thus, for light entering the reception side polarization separation element $22_1$, that is, the light in the predetermined wavelength band which is longer than 870 nm and shorter than 1,000 nm and which contains the above-described predetermined wavelength band $B_1$, the reception side polarization separation element $22_1$ transmits only the P-polarized light, which is perpendicular to the S-polarized light transmitted through the irradiation side polarization separation element $21_1$ (reference character P parenthesized in FIG. 14B indicates that the reception side polarization separation element $22_1$ actually transmits the P-polarized light in connection with the location).

The image processing device (processor) 3 has a control section 31, a video signal circuit 32, and an image operation device 33. The control section 31 performs driving control such that the rotary filter 12 is set in the optical path by a movement stage (net shown in the drawings), in response to a specification of the non polarization observation mode or polarization observation mode, switched via a mode switch (not shown in the drawings). The control section 31 controls rotational driving of the motor 12f, which rotates the rotary filter 12. The control section 31 further performs predetermined driving control on the image pickup element $22_2$ and the video signal circuit 32 (and the image operation device 33). The video signal circuit 32 converts optical information obtained by the image pickup element $22_2$ into a digital signal (image data). The video signal circuit 32 converts the digital data into analog data and then feeds the analog data to the monitor 4. The image operation device 33 executes a predetermined arithmetic process on the image data converted into the digital signal via the video signal circuit 32, according to a set mode. For example, for the non polarization observation mode, the image operation device 33 adds the image components of R, G, and B together and then outputs the result. For the polarization observation mode, the image operation device 33 determines the difference between the polarized image components picked up in the predetermined wavelength band to output the resultant difference component. The predetermined arithmetic process executed by the image operation device 33 is not limited to the above-described one. A desired arithmetic process may be set via predetermined setting means. The monitor 4 displays the image data subjected to image processing by the processor 3.

Observation using the endoscope observation system in Example 1 configured as described above will be described. When the polarization observation mode is specified, the control section 31 allows the movement stage (not shown in the drawings) to move the rotary filter 12 so as to position the polarization observation filters (the outer peripheral filters 12d and 12e of the rotary filter 12) on the illumination optical path. Then, the rotary filter 12 is rotated via the motor 12f. The light source 11 emits light, and light in the predetermined wavelength band $A_1$, which is longer than 700 nm and shorter than 870 nm and light in the predetermined wavelength band $B_1$, which is longer than 870 nm and shorter than 1000 nm, sequentially pass through the polarization observation filters 12d and 12e of the rotary filter 12, and sequentially enter the light guide $21_2$ via the condensing lens 13.

The light in the predetermined wavelength band $A_1$ and the light in the predetermined wavelength band $B_1$ having sequentially entered the light guide $21_2$ enter the irradiation side polarization separation element $21_1$ via the lens $21_3$. In this case, the irradiation side polarization separation element $21_1$ has the property of transmitting only the S-polarized light for light in a predetermined wavelength band which is longer than 700 nm and shorter than 1,000 nm and which contains the predetermined wavelength bands $A_1$ and $B_1$. Thus, for both the light in the predetermined wavelength band $A_1$ and the light in the predetermined wavelength band $B_1$, only the S polarization component passes through the irradiation side polarization separation element $21_1$. The light with the S polarization component transmitted through the irradiation side polarization separation element $21_1$ impinges on an observation target 5 via the illumination lens $21_4$.

Part of reflected light from the observation target 5 enters the reception side polarization separation element $22_1$ via the objective lens $22_3$ and the image forming lens $22_4$. In this case, the light reflected by the observation target 5 contains light with an S polarization component II reflected by the surface of the observation target 5 and having the same polarization condition as that of an irradiated S polarization component I, and light with an S polarization component III and a P polarization component IV with the polarization condition disturbed by scattering in a deep layer portion. For the incident light in the predetermined wavelength band $A_1$, which is longer than 700 nm and shorter than 870 nm, all of the S polarization components II and III and the P polarization component IV pass through the reception side polarization separation element $22_1$. On the other hand, for the incident light in the predetermined wavelength band $B_1$, which is longer than 870 nm and shorter than 1,000 nm, only the P polarization component IV passes through the reception side polarization separation element $22_1$ and not the S polarization components II and III. This is because the reception side polarization separation element $22_1$ is located so as to rotate the polarization direction of the S polarization component through 90 degrees which is transmitted through the reception side polarization separation element $22_1$ as described above. Thus, the light in the predetermined wavelength band $B_1$ is separated into the P and S polarization components.

The image pickup element $22_2$ sequentially picks up images of the light in the predetermined wavelength band $A_1$ and the light in the predetermined wavelength band $B_1$ transmitted through the reception side polarization separation element $22_1$. The optical information obtained by the image pickup element $22_2$ is converted into a digital signal (image data) via the video signal circuit 32. The image operation device 33 subjects the resulting image data to, for example, the following image processing. As described above, the P and S polarization components IV and III of scattering light are expected to have substantially the same light intensity. Thus, the intensity of the scattering light in the deep layer of the living body is determined from a P polarization component IV×2 obtained for the light in the predetermined wavelength band $B_1$. Furthermore, the S polarization component II is determined by subtracting the P polarization component IV×2 obtained for the light in the predetermined wavelength band $B_1$, which is longer than 870 nm and shorter than 1,000 nm, from the non polarized image data made up of the S polarization components I and II and the P polarization component IV obtained for the light in the predetermined wavelength band $A_1$, which is longer than 700 nm and shorter than 870 nm. Consequently, the image of the S-polarized light reflected by the cortical layer in the living body can be exclusively calculated. The image only of the cortical layer can thus foe observed via the monitor 4.

On the other hand, to allow for observation in the son polarization observation mode, the control section 31 allows the movement stage (not shown in the drawings) to move the rotary filter 12 so as to position the non polarization observation filters (the inner peripheral filters 12a, 12b, and 12c of the rotary filter 12) on the illumination optical path. Then, the rotary filter 12 is rotated via the motor 12f. The light source 11 emits light, and light of R, light of G, and light of B sequentially pass through the non polarization observation filters 12a, 12b, and 12c of the rotary filter 12 to sequentially enter the light guide $21_2$ via the condensing lens 13. The light of R, the light of G, and the light of B having sequentially entered the light guide $21_2$ enter the irradiation side polarization separation element $21_1$ via the lens $21_3$. In this case, the irradiation side polarization separation element $21_1$ has the property of transmitting all of the P-polarized light, the S-polarized light, and the non polarized light for light in a predetermined wavelength band which is shorter than 700 nm and which contains the wavelength bands of R, G, and B. Thus, all of the light of R, the light of G, and the light of B pass through the irradiation side polarization separation element $21_1$ in a non polarized condition with the quantity of light prevented from being cut.

The light of R, light of G, and light of B transmitted through the irradiation side polarization separation element $21_1$ impinge on the observation target 5 via the illumination lens $21_4$. Part of reflected light from the observation target 5 enters the reception side polarization separation element $22_1$ via the objective lens $22_3$ and the image forming lens $22_4$. In this case, the reception side polarization separation element $22_1$ has the property of transmitting all of the P-polarized light, the S-polarized light, and the non polarized light for light in a predetermined wavelength band which is shorter than 870 nm and which contains the wavelength bands of R, G, and B. Thus, all of the light of R, the light of G, and the light of B pass through the reception side polarization separation element $22_1$ in the non polarized condition with the quantity of light prevented from being cut. The image pickup element $22_2$ sequentially picks up images of the light of R, the light of G, and the light of B transmitted through the reception side polarization separation element $22_1$. The optical information obtained by the image pickup element $22_2$ is converted into a digital signal (image data) via the video signal circuit 32. The image operation circuit 33 subjects the resulting image data to image processing by, for example, adding image components for R, G, and B together and outputting the result of the addition. Thus, a non polarization observation image is obtained with a possible decrease in the quantity of light prevented without the need to retract the polarization separation element $22_1$ from the optical path.

Thus, according to the endoscope observation system in Example 1, the brightness of the irradiation light in the observation mode other than the polarization observation mode is substantially similar to that of illumination light provided by an illumination optical system configured without a polarizer. Furthermore, in the observation mode other than the polarization observation mode, the quantity of illumination light is prevented from being reduced by the polarization. This enables an increase in the diameters of the illumination optical system and the image pickup optical system to be prevented without the need for a mechanical structure for switching the polarization member. Furthermore, the illumination light can be provided in the non polarization observation mode based on visible light and in the polarization observation mode in an infrared region using the same illumination optical system, while minimizing a decrease in the quality of observation light for the observation based on the normal light.

Furthermore, according to the endoscope observation system in Example 1, the illumination light in the polarization observation mode is made up of two types of light in the different wavelength bands. Consequently, information on scattering in the living body and on the cortical layer can be obtained as follows. The observation target is irradiated with polarized illumination light in two different wavelength bands. The image pickup optical system picks up an image of the irradiation light in one of the wavelength bands reflected by the observation target without change (light with the polarization condition unchanged and light with the polarization condition disturbed). The image pickup optical system separates the irradiation light in the other wavelength band into the light with the polarization condition unchanged and the light with the polarization condition disturbed. The image pickup optical system then picks up an image of the light with the polarization condition disturbed. Then, images obtained from the illumination light in the respective wavelength bands are compared with each other. The other effects of the endoscope observation system in Example 1 are almost the same as those of the endoscope observation systems according to the first and second embodiments.

Example 2

Figure 16A:
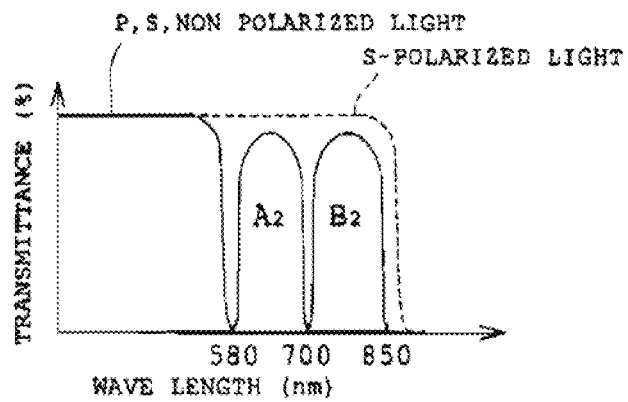
Figure 16B:
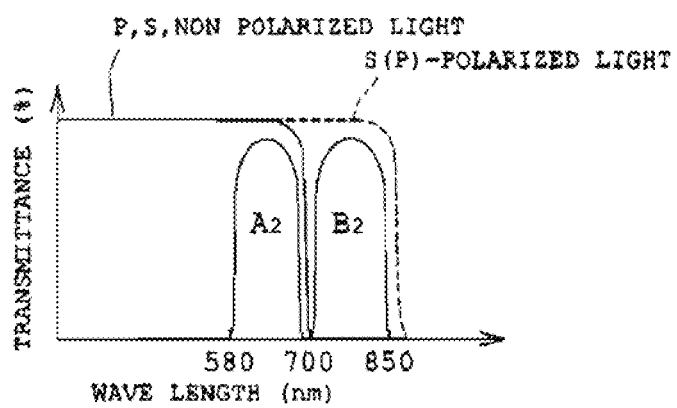
Figure 16C:
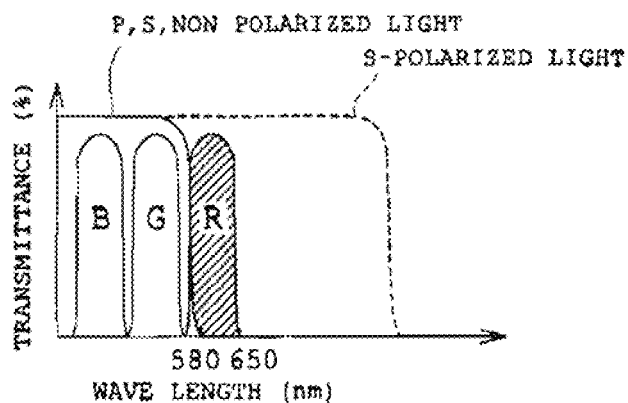

FIGS. 16A, 16B, and 16C are graphs showing the characteristics of wavelength bands and optical elements for light used in an endoscope observation system in Example 2 of the present invention. FIG. 16A shows the transmission characteristics (two wavelength bands used as illumination light in the polarization observation mode) of two filters for the polarization observation mode which are provided in a light source section, and the transmission characteristics (the transmission wavelength bands of S-polarized light, P-polarized light, and non polarized light) of a polarization separation element provided in an illumination optical system. FIG. 16B shows two wavelength bands used as illumination light in the polarization observation mode and the transmission characteristics (the transmission wavelength bands of S-polarized light, P-polarized light, and non polarized light) of a polarization separation element provided in an image pickup optical system. FIG. 16C shows transmission characteristics (in this case, the wavelength bands of R (Red), G (Green), and B (Blue) used as illumination light in the non polarization observation mode) of a filter for the non polarization observation mode which is provided in the light source section, and the transmission characteristics (the wavelength bands of S-polarized light, P-polarized light, and non polarized light) of the polarization separation element provided in the illumination optical system. The general configuration of the endoscope observation system in Example 2 is substantially the same as that of the endoscope observation system in Example 1 shown in FIG. 12. Here, only components different from those in Example 1 will be described. Furthermore, the configuration in FIG. 12 will be referenced as required.

In the endoscope observation system in Example 2, the characteristics of polarization observation filters 12d and 12e of a rotary filter 12, an irradiation side polarization separation element $21_1$, and a reception side polarization separation element $22_1$ are as follows. Filters 12d and 12e as polarization observation filters are provided on the outer periphery side of the rotary filter 12 so that the rotary filter 12 is divided into the two pieces in the circumferential direction; as shown in FIG. 16A the filter 12d has the property of transmitting only light in a predetermined wavelength band $A_2$ longer than 580 nm and shorter than 700 nm, and the filter 12e has the property of transmitting only light in a predetermined wavelength band $B_2$ longer than 700 nm and shorter than 850 nm.

The irradiation side polarization separation element $21_1$ is composed of a prism type polarization beam splitter with a dichroic coat applied thereto. As shown in FIG. 16A, the irradiation side polarization separation element $21_1$ has the property of transmitting all of the P-polarized light, the S-polarized light, and the non polarized light for light in a predetermined wavelength band which is shorter than 580 nm and which contains the wavelength bands of G and B, while transmitting only the S-polarized light for light in a predetermined wavelength band which is longer than 580 nm and shorter than 850 nm and which contains the above-described predetermined wavelength bands $A_2$ and $B_2$.

The reception side polarization separation element $22_1$ is composed of a prism type polarization beam splitter with a dichroic coat applied thereto. As shown in FIG. 16B, the reception side polarization separation element $22_1$ has the property of transmitting all of the P-polarized light, the S-polarized light, and the non polarized light for light in a predetermined wavelength band which is shorter than 700 nm and which contains the above-described predetermined wavelength $A_2$ and the wavelength bands of G and B, while transmitting only the S-polarized light for light in a predetermined wavelength band which is longer than 700 nm and shorter than 850 nm and which contains the above-described predetermined wavelength band $B_2$. Furthermore, the reception side polarization separation element $22_1$ is located so as to rotate the transmitted light through 90 degrees so that the polarization direction of the polarization component (S-polarized light) transmitted in the polarization separation wavelength band (that is, the predetermined wavelength baud which is longer than 700 nm and shorter than 850 nm and which contains the above-described predetermined wavelength band $B_2$) is orthogonal to the polarization direction of the polarization component (S-polarized light) transmitted in the polarization separation wavelength band of the irradiation side polarization separation element $21_1$ (that is, the predetermined wavelength band which is longer than 580 nm and shorter than 850 nm and which contains the above-described predetermined wavelength bands $A_2$ and $B_2$) (this is not shown in the drawings).

Thus, for light entering the reception side polarization separation element $22_1$, that is, the light in the predetermined wavelength band which is longer than 700 nm and shorter than 850 nm and which contains the above-described predetermined wavelength band $B_2$, the reception side polarization separation element $22_1$ transmits only the P-polarized light, which is perpendicular to the S-polarized light transmitted through the irradiation side polarization separation element $21_1$ (reference character P parenthesized in FIG. 16B indicates that the reception side polarization separation element $22_1$ actually transmits the P-polarized light in connection with the location). The remaining part of the configuration of the endoscope observation system is almost the same as that of the endoscope observation system in Example 1.

Observation using the endoscope observation system in Example 2 configured as described above will be described. When the polarization observation mode is specified, a control section 31 allows a movement stage (not shown in the drawings) to move the rotary filter 12 so as to position the polarization observation filters (outer peripheral filters) on the illumination optical path. Then, the rotary filter 12 is rotated via a motor 12f. When a light source 11 emits light, light in the predetermined wavelength band $A_2$, which is longer than 580 nm and shorter than 700 nm, and light in a predetermined wavelength band $B_2$, which is longer than 700 nm and shorter than 850 nm, sequentially pass through the polarization observation filters of the rotary filter 12, and sequentially enter a light guide $21_2$ via a condensing lens 13. The light in the predetermined wavelength band $A_2$ and the light in the predetermined wavelength band $B_2$ having sequentially entered the light guide $21_2$ enter the irradiation side polarization separation element $21_1$ via a lens $21_3$. In this case, the irradiation side polarization separation element $21_1$ has the property of transmitting only the S-polarized light for light in a predetermined wavelength band which is longer than 580 nm and shorter than 850 nm and which contains the predetermined wavelength bands $A_2$ and $B_2$. Thus, for both the light in the predetermined wavelength band $A_2$ and the light in the predetermined wavelength band $B_2$, only the S polarization component passes through the irradiation side polarization separation element $21_1$. The light with the S polarization component transmitted through the irradiation side polarization separation element $21_1$ impinges on an observation target 5 via an illumination lens $21_4$.

Part of reflected light from the observation target 5 enters the reception side polarization separation element $22_1$ via an objective lens $22_3$ and an image forming lens $22_4$ of the image pickup optical system 22. In this case, the light reflected by the observation target 5 contains light with an S polarization component II reflected by the surface of the observation target 5 and having the same polarization condition as that of an irradiated S polarization component I, and light with an S polarization component III and a P polarization component IV with the polarization condition disturbed by scattering in the deep layer portion. For the incident light in the predetermined wavelength band $A_2$, which is longer than 580 nm and shorter than 700 nm, all of the S polarization components II and III and the P polarization component IV pass through the reception side polarization separation element $22_1$. On the other hand, for the incident light in the predetermined wavelength band $B_2$, which is longer than 700 nm and shorter than 850 nm, only the P polarization component IV passes through the reception side polarization separation element $22_1$ and not the S polarization components II and III. This is because the light in the predetermined wavelength band $B_2$ is oriented by rotating the polarization direction of the S polarization component through 90 degrees which is transmitted through the reception side polarization separation element $22_1$ as described above. Thus, the light in the predetermined wavelength band $B_2$ is separated into the P and S polarization components.

The image pickup element $22_2$ sequentially picks up images of the light in the predetermined wavelength band $A_2$ and the light in the predetermined wavelength band $B_2$ transmitted through the reception side polarization separation element $22_1$. The optical information obtained by the image pickup element $22_2$ is converted into a digital signal (image data) via a video signal circuit 32. An image operation device 33 subjects the resulting image data to, for example, the following image processing. As described above, the P and S polarization components IV and III of scattering light are expected to have substantially the same light intensity. Thus, the intensity of the scattering light in the deep layer of the living body is determined from a P polarization component IV×2 obtained for the light in the predetermined wavelength band $B_2$. Furthermore, the S polarization components II is determined by subtracting the P polarization component IV×2 obtained for the light in the predetermined wavelength band $B_2$, which is longer than 700 nm and shorter than 850 nm, from the non polarized image data made up of the S polarization components I and II and the P polarization component IV obtained for the light in the predetermined wavelength band $A_2$, which is longer than 580 nm and shorter than 700 nm. Consequently, the image at the S-polarized light reflected by the cortical layer in the living body can be exclusively calculated. The image only of the cortical layer can thus be observed via a monitor 4.

On the other hand, to allow for observation in the non polarization observation mode, the control section 31 allows the movement stage (not shown in the drawings) to move the rotary filter 12 so as to position the non polarization observation filters (inner peripheral filters) on the illumination optical path. Then, the rotary filter 12 is rotated via the motor 12f. The light source 11 emits light, and light of R, light of G, and light of B sequentially pass through non polarization observation filters 12a, 12b, and 12c of the rotary filter 12 to sequentially enter the light guide $21_2$ via the condensing lens 13.

The light of R, the light of G, and the light of B having sequentially entered the light guide $21_2$ enter the irradiation side polarization separation element $21_1$ via the lens $21_3$. In this case, the irradiation side polarization separation element $21_1$ has the property of transmitting all of the P-polarized light, the S-polarized light, and the non polarized light for light in a predetermined wavelength band which is shorter than 580 nm and which contains the wavelength bands of G and B, while transmitting only the S-polarized light for light in a predetermined wavelength band which is longer than 580 nm and shorter than 850 nm and which contains the wavelength band of R. Thus, of the light of R, the light of G, and the light of B, the light of G and the light of B pass through the irradiation side polarization separation element $21_1$ in the non polarized condition with the quantity of light prevented from being cut. Only the light of R is reduced to half and passes through the irradiation side polarization separation element $21_1$ in a polarized condition. The non polarized light of G and B and the S-polarized light of R transmitted through the irradiation side polarization separation element $21_1$ impinge on the observation target 5 via the illumination lens $21_4$. Part of reflected light from the observation target 5 enters the reception side polarization separation element $22_1$ via the objective lens $22_3$ and the image forming lens $22_4$ of the image pickup optical system 22.

In this case, the reception side polarization separation element $22_1$ has the property of transmitting all of the P-polarized light, the S-polarized light, and the non polarized light for light in a predetermined wavelength band which is shorter than 700 nm and which contains the wavelength bands of R, G, and B. Thus, all of the non polarized light of G and B and the S-polarized light of R pass through the reception side polarization separation element $22_1$ with the quantity of light prevented from being cut. The image pickup element $22_2$ sequentially picks up images of the non polarized light of G and B and the S-polarized light of R transmitted through the reception side polarization separation element $22_1$. The optical information obtained by the image pickup element $22_2$ is converted into a digital signal (image data) via the video signal circuit 32. The image operation device 33 subjects the resulting image data to image processing by, for example, adding image components for R, G, and B together and outputting the result of the addition. Thus, a non polarization observation image is obtained with a possible sharp reduction in the quantity of light prevented without the need to retract the polarization separation element $22_1$ from the optical path.

Thus, according to the endoscope observation system in Example 2, the intensity obtained from the irradiation light of R by the image pickup element is reduced to half. However, the quantity of light resulting from the irradiation light of G and B is prevented from being cut, with this level of decrease in the quantity of light, the observation can be prevented from being affected, by for example, adjusting gain or removing a color correction filter to provide color tones that do not affect the observation. Thus, the endoscope observation system enables an increase in the diameters of the illumination optical system and the image pickup optical system to be prevented without the need for a mechanical switching structure. The endoscope observation system also allows the illumination light to be applied in the non polarization observation mode based on the visible light and the polarization observation mode in a yellow to red region and the infrared region using the same illumination optical system, while minimizing a decrease in the quantity of light for the non polarized light-based observation. The other effects are almost the same as those of the endoscope observation system in Example 1.

Example 3

Figure 17A:
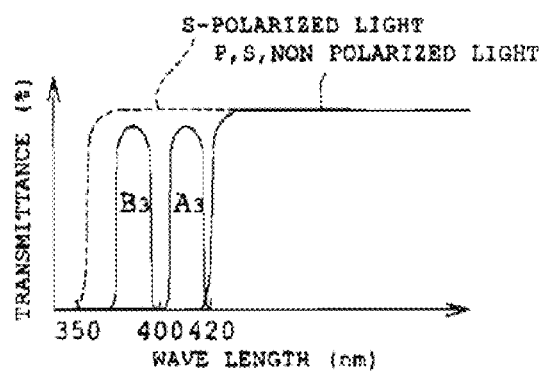
Figure 17B:
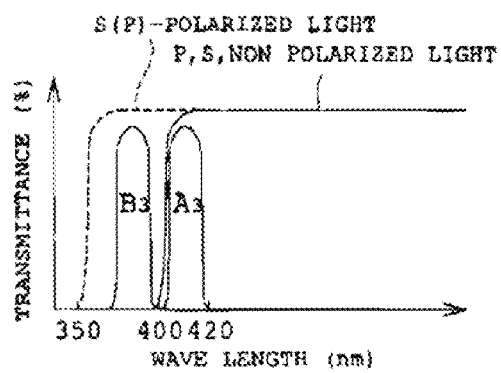

FIGS. 17A and 17B are graphs showing the characteristics of wavelength bands and optical elements for light used in an endoscope observation system in Example 3 of the present invention. FIG. 17A shows the transmission characteristics (two wavelength bands used as illumination light in the polarization observation mode) of two filters for the polarization observation mode which are provided in a light source section, and the transmission characteristics (the transmission wavelength bands of S-polarized light, P-polarized light, and non polarized light) of a polarization separation element provided in an illumination optical system. FIG. 17B shows two wavelength bands used as illumination light in the polarization observation mode and the transmission characteristics (the transmission wavelength bands of S-polarized light, P-polarized light, and non polarized light) of a polarization separation element provided in an image pickup optical system. The general configuration of the endoscope observation system in Example 3 is substantially the same as that of the endoscope observation system in Example 1 shown in FIG. 12. Here, only components different from those in Example 1 will be described. Furthermore, the configuration in FIG. 12 will be referenced as required. In the endoscope observation system in Example 3, the characteristics of polarization observation filters 12d and 12e of a rotary filter 12, an irradiation side polarization separation element $21_1$, and a reception side polarization separation element $22_1$ are as follows.

Filters 12d and 12e as polarization observation filters are provided on the outer periphery side of the rotary filter 12 so that the rotary filter 12 is divided into the two pieces in the circumferential direction; as shown in FIG. 17A, the filter 12d has the property of transmitting only light in a predetermined wavelength band $B_3$ longer than 350 nm and shorter than 400 nm, and the filter 12e has the property of transmitting only light in a predetermined wavelength band $A_3$ longer than 400 nm and shorter than 420 nm. The irradiation side polarization separation element $21_1$ is composed of a prism type polarization beam splitter with a dichroic coat applied thereto. As shown in FIG. 17A, the irradiation side polarization separation element $21_1$ has the property of processing the illumination light from the light source section 1 by transmitting only the S-polarized light for light in a predetermined wavelength band which is longer than 350 nm and shorter than 420 nm and which contains the wavelength bands $B_3$ and $A_3$, while transmitting all of the P-polarized light, the S-polarized light, and the non polarized light for light in a predetermined wavelength band which is longer than 420 nm and which contains the wavelength bands of R, G, and B.

The reception side polarization separation element $22_1$ is composed of a prism type polarization beam splitter with a dichroic coat applied thereto. As shown in FIG. 17B, the reception side polarization separation element $22_1$ has the property of transmitting only the S-polarized light for light in a predetermined wavelength band which is longer than 350 nm and shorter than 400 nm and which contains the predetermined wavelength band $B_3$, while transmitting all of the P-polarized light, the S-polarized light, and the non polarized light for light in a predetermined wavelength band which is longer than 400 nm and which contains the predetermined wavelength band $A_3$ and the wavelength bands of R, G and B. Furthermore, the reception side polarization separation element $22_1$ is located so as to rotate the transmitted light through 90 degrees so that the polarization direction of the polarization component (S-polarized light) transmitted in the polarization separation wavelength band (that is, the predetermined wavelength band which is longer than 350 nm and shorter than 400 nm and which contains the above-described predetermined wavelength band $B_3$) is orthogonal to the polarization direction of the polarization component (S-polarized light) transmitted in the polarization separation wavelength band of the irradiation side polarization separation element $21_1$ (that is, the predetermined wavelength band which is longer than 350 nm and shorter than 420 nm and which contains the above-described predetermined wavelength bands $A_3$ and $B_3$) (this is not shown in the drawings).

Thus, for light entering the reception side polarization separation element $22_1$, that is, the light in the predetermined wavelength band which is longer than 350 nm and shorter than 400 nm and which contains the above-described predetermined wavelength band $B_3$, the reception side polarization separation element $22_1$ transmits only the P-polarized light, which is perpendicular to the S-polarized light transmitted through the irradiation side polarization separation element $21_1$ (reference character P parenthesized in FIG. 17B indicates that the reception side polarization separation element $22_1$ actually transmits the P-polarized light in connection with the location). The remaining part of the configuration of the endoscope observation system is almost the same as that of the endoscope observation system in Example 1.

Observation using the endoscope observation system in Example 3 configured as described above will be described, when the polarization observation mode is specified, a control section 31 allows a movement stage (not shown in the drawings) to move the rotary filter 12 so as to position the polarization observation filters (outer peripheral filters) on the illumination optical path. Then, the rotary filter 12 is rotated via a motor 12f. When a light source 11 emits light, light in the predetermined wavelength band $B_3$, which is longer than 350 nm and shorter than 400 nm, and light in a predetermined wavelength band $A_3$, which is longer than 400 nm and shorter than 420 nm, sequentially pass through the polarization observation filters of the rotary filter 12, and sequentially enter a light guide $21_2$ via a condensing lens 13. The light in the predetermined wavelength band $B_3$ and the light in the predetermined wavelength band $A_3$ having sequentially entered the light guide $21_2$ enter the irradiation side polarization separation element $21_1$ via a lens $21_3$.

In this case, the irradiation side polarization separation element $21_2$ has the property of transmitting only the S-polarized light for light in a predetermined wavelength band which is longer than 350 nm and shorter than 420 nm and which contains the above-described predetermined wavelength bands $B_3$ and $A_3$. Thus, for both the light in the predetermined wavelength band $B_3$ and the light in the predetermined wavelength band $A_3$, only the S polarization component passes through the irradiation side polarization separation element $21_1$. The light with the S polarization component transmitted through the irradiation side polarization separation element $21_1$ impinges on an observation target 5 via an illumination lens $21_4$. Part of reflected light from the observation target 5 enters the reception side polarization separation element $22_1$ via an objective lens $22_3$ and an image forming lens $22_4$ of the image pickup optical system 22. In this case, the light reflected by the observation target 5 contains light with an S polarization component II reflected by the surface of the observation target 5 and having the same polarization condition as that of an irradiated S polarization component I, and light with an S polarization component III and a P polarization component IV with the polarization condition disturbed by scattering in the deep layer portion.

For the incident light in the predetermined wavelength band $A_3$, which is longer than 400 nm and shorter than 420 nm, all of the S polarization components II and III and the P polarization component IV pass through the reception side polarization separation element $22_1$. On the other hand, for the incident light in the predetermined wavelength band $B_3$, which is longer than 350 nm and shorter than 400 nm, only the P polarization component IV passes through the reception side polarization separation element $22_1$ and not the S polarization components II and III. This as because the light in the predetermined wavelength band $B_3$ is oriented by rotating the polarization direction of the S polarization component through 90 degrees which is transmitted through the reception side polarization separation element $22_1$ as described above. Thus, the light in the predetermined wavelength band $B_3$ is separated into the P and S polarization components. The image pickup element $22_2$ sequentially picks up images of the light in the predetermined wavelength band $A_3$ and the light in the predetermined wavelength band $B_3$ transmitted through the reception side polarization separation element $22_1$.

The optical information obtained by the image pickup element $22_2$ is converted into a digital signal (image data) via a video signal circuit 32. The image operation device 33 subjects the resulting image data to, for example, the following image processing. As described above, the P and S polarization components IV and III of scattering light are expected to have substantially the same light intensity. Thus, the intensity of the scattering light in the deep layer of the living body is determined from a P polarization component IV×2 obtained for the light in the predetermined wavelength band $B_3$. Furthermore, the S polarization component II is obtained by determining the difference between the non polarized image data made up of the S polarization components II and III and the P polarization component IV obtained for the light in the predetermined wavelength band $A_3$, which is longer than 400 nm and shorter than 420 nm, and the P polarization component IV×2 obtained for the light in the predetermined wavelength band $B_3$, which is longer than 350 nm and shorter than 400 nm. Consequently, the image of the S-polarized light reflected by the cortical layer in the living body can be exclusively calculated. The image only of the cortical layer can thus be observed via a monitor 4.

On the other hand, to allow for observation in the non polarization observation mode, the control section 31 allows the movement stage (not shown in the drawings) to move the rotary filter 12 so as to position the non polarization observation filters (the inner peripheral filters) on the illumination optical path. Then, the rotary filter 12 is rotated via the motor 12f. The light source 11 emits light, and light of R, light of G, and light of B sequentially pass through non polarization observation filters 12a, 12b, and 12c of the rotary filter 12 to sequentially enter the light guide $21_2$ via the condensing lens 13. The light of R, the light of G, and the light of B having sequentially entered the light guide $21_2$ enter the irradiation side polarization separation element $21_1$ via the lens $21_3$. In this case, the irradiation side polarization separation element $21_1$ has the property of transmitting all of the P-polarized light, the S-polarized light, and the non polarized light for light in a predetermined wavelength band which is longer than 420 nm and which contains the wavelength bands of R, G, and B. Thus, all of the light of R, the light of G, and the light of B pass through the irradiation side polarization separation element $21_1$ in the non polarized condition with the quantity of light prevented from being cut.

The light of R, the light of G, and the light of B transmitted through the irradiation side polarization separation element $21_1$ impinge on the observation target 5 via the illumination lens $21_4$. Part of reflected light from the observation target 5 enters the reception side polarization separation element $22_1$ via the objective lens $22_3$ and the image forming lens $22_4$ of the image pickup optical system 22. In this case, the reception side polarization separation element $22_1$ has the property of transmitting all of the P-polarized light, the S-polarized light, and the non polarized light for light in a predetermined wavelength band which is longer than 400 nm and which contains the wavelength bands of R, G, and B. Thus, all of the light of R, the light of G, and the light of B pass through the reception side polarization separation element $22_1$ in the non polarized condition with the quantity of light prevented from being cut. The image pickup element $22_2$ sequentially picks up images of the light of R, the light of G, and the light of B transmitted through the reception side polarization separation element $22_1$. The optical information obtained by the image pickup element $22_2$ is converted into a digital signal (image data) via the video signal circuit 32. The image operation device 33 subjects the resulting image data to image processing by, for example, adding image components for R, G, and B together and outputting the result of the addition. Thus, a non polarization observation image is obtained with a possible reduction in the quantity of light prevented without the need to retract the polarization separation element $22_1$ from the optical path.

Thus, according to the endoscope observation system in Example 3, the brightness of the irradiation light in the observation mode other than the polarization observation mode is substantially similar to that of illumination light provided by an illumination optical system configured without a polarizer. Furthermore, in the observation mode other than the polarization observation mode, the quantity of illumination light is prevented from being reduced by the polarization. Thus, the endoscope observation system enables an increase in the diameters of the illumination optical system and the image pickup optical system to be prevented without the need for a mechanical structure for switching the polarization member. The endoscope observation system also allows the illumination light to be applied in the non polarization observation mode based on the visible light and the polarization observation mode in an ultraviolet to violet region using the same illumination optical system, while minimizing a decrease in the quantity of observation light for the observation based on the normal light. The other effects are almost the same as those of the endoscope observation system in Example 1.

Example 4

Figure 18A:
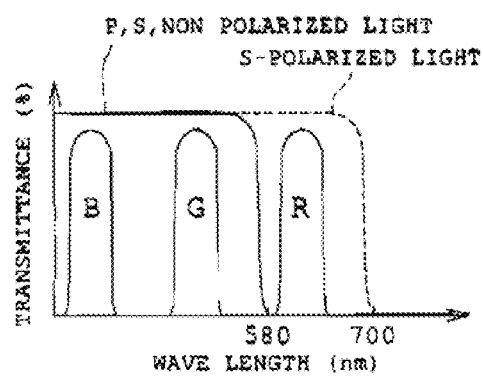
Figure 18B:
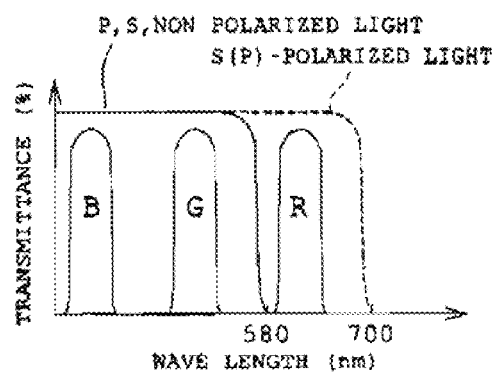

FIGS. 18A and 18B are graphs showing the characteristics of wavelength bands and optical elements for light used in an endoscope observation system in Example 4 of the present invention. FIG. 18A shows the transmission characteristics (three wavelength bands used as illumination light in the polarization observation mode) of three filters for the polarization observation mode which are provided in a light source section, and the transmission characteristics (the transmission wavelength bands of S-polarized light, P-polarized light, and non polarized light) of a polarization separation element provided in an illumination optical system. FIG. 18B shows three wavelength bands used as illumination light in the polarization observation mode and the transmission characteristics (the transmission wavelength bands of S-polarized light, P-polarized light, and non polarized light) of a polarization separation element provided in an image pickup optical system. The general configuration of the endoscope observation system in Example 4 is substantially the same as that of the endoscope observation system in Example 1 shown in FIG. 12. Here, only components different from those in Example 1 will be described. Furthermore, the configuration in FIG. 12 will be referenced as required.

The endoscope observation system in Example 4 is configured to pick up a scattering image using, for the polarization observation, the light in the wavelength band of red (R) and not the light in the two other wavelength bands and to simultaneously pick up an image of an observation target that is capillary vessels silhouetted by NBI (Narrow Band imaging). The characteristics of an irradiation side polarization separation element $21_1$ and a reception side polarization separation element $22_1$ are as follows. The irradiation side polarization separation element $21_1$ is composed of a prism type polarization beam splitter with a dichroic coat applied thereto. As shown in FIG. 18A, the irradiation side polarization separation element $21_1$ has the property of processing the illumination light from the light source section 1 by transmitting all of the P-polarized light, the S-polarized light, and the non polarized light for light in a predetermined wavelength band which is shorter than 580 nm and which contains the wavelength bands of G and B, while transmitting only the S-polarized light for light in a predetermined wavelength band which is longer than 580 nm and shorter than 700 nm and which contains the wavelength band of R.

The reception side polarization separation element $22_1$ is composed of a prism type polarization beam splitter with a dichroic coat applied thereto. As shown in FIG. 18B, the reception side polarization separation element $22_1$ has the property of transmitting all of the P-polarized light, the S-polarized light, and the non polarized light for light in a predetermined wavelength band which is shorter than 580 nm and which contains the wavelength bands of G and B, while transmitting only the S-polarized light for light in a predetermined wavelength band which is longer than 580 nm and shorter than 700 nm and which contains the wavelength band of R. Furthermore, the reception side polarization separation element $22_1$ is located so as to rotate the transmitted light through 90 degrees so that the polarization direction of the polarization component (S-polarized light) transmitted in the polarization separation wavelength band (that is, the predetermined wavelength band which is longer than 580 nm and shorter than 700 nm and which contains the above-described wavelength band of R) is orthogonal to the polarization direction of the polarization component (S-polarized light) transmitted in the polarization separation wavelength band of the irradiation side polarization separation element $21_1$ (that is, the predetermined wavelength band which is longer than 580 nm and shorter than 700 nm and which contains the above-described wavelength band of R) (this is not shown in the drawings).

Thus, for light entering the reception side polarization separation element $22_1$, that is, the light in the predetermined wavelength band which is longer than 580 nm and shorter than 700 nm and which contains the above-described wavelength band of R, the reception side polarization separation element $22_1$ transmits only the P-polarized light, which is perpendicular to the S-polarized light transmitted through the irradiation side polarization separation element $21_1$ (reference character P parenthesized in FIG. 18B indicates that the reception side polarization separation element $22_1$ actually transmits the P-polarized light in connection with the location). Furthermore, an R filter 12a, a G filter 12b, and a B filter 12c are arranged on the outer and inner peripheries of a rotary filter 12 so that the rotary filter 12 is divided into the three pieces in the circumferential direction; the R filter 12a, the G filter 12b, and the B filter 12c have the properties of transmitting light in the wavelength bands of R, G, and B, respectively. The remaining part of the configuration of the endoscope observation system is almost the same as that of the endoscope observation system in Example 1.

Observation using the endoscope observation system in Example 4 configured as described above will be described. A light source 11 emits light, and light of R, light of G, and light of B sequentially pass through the rotary filter 12 to sequentially enter a light guide $21_2$ via a condensing lens 13. The light of R, the light of G, and the light of B having sequentially entered the light guide $21_2$ enter the irradiation side polarization separation element $21_1$ via a lens $21_3$. In this case, the irradiation side polarization separation element $21_1$ has the property of transmitting all of the P-polarized light, the S-polarized light, and the non polarized light for light in a predetermined wavelength band which is shorter than 580 nm and which contains the wavelength bands of G and B, while transmitting only the S-polarized light for light in a predetermined wavelength band which is longer than 580 nm and shorter than 700 nm and which contains the wavelength band of R. Thus, of the light of R, the light of G, and the light of B, the light of G and the light of B pass through the irradiation side polarization separation element $21_1$ in the non polarized condition with the quantity of light prevented from being cut. Only the light of R is cut to half, with only the S polarization component passing through the irradiation side, polarization separation element $21_1$. The non polarized light of G and B and the S-polarized light of R transmitted through the irradiation side polarization separation element $21_1$ impinge on the observation target 5 via an illumination lens $21_4$.

Part of reflected light from the observation target 5 enters the reception side polarization separation element $22_1$ via the objective lens $22_3$ and the image forming lens $22_4$ of the image pickup optical system 22. In this case, the light of R reflected by the observation target 5 contains light with an S polarization component II reflected by the surface of the observation target 5 and having the same polarization condition as that of an irradiated S polarization component I, and light with an S polarization component III and a P polarization component iv with the polarization condition disturbed by scattering in the deep layer portion. The light of G and the light of B reflected by the observation target 5 are in the non polarized condition. In this case, the reception side polarization separation element $22_1$ has the property of transmitting all of the P-polarized light, the S-polarized light, and the non polarized light for light in a predetermined wavelength band which is shorter than 580 nm and which contains the wavelength bands of B and G. Thus, both the light of G and the light of B pass through the reception side polarization separation element $22_1$ in the non polarized condition with the quantity of light prevented from being cut.

The reception side polarization separation element $22_1$ also has the property of transmitting only the S-polarized light for light in a predetermined wavelength band which is longer than 580 nm and shorter than 700 nm and which contains the wavelength band of R. Furthermore, the reception side polarization separation element $22_1$ is located so as to rotate the polarization direction of the polarized light (S-polarized light) through 90 degrees which is transmitted through the reception side polarization separation element $22_1$ as described above. Thus, for the light in the predetermined wavelength band which is longer than 580 nm and shorter than 700 nm and which contains the wavelength band of R, only the P polarization component IV passes through the reception side polarization separation element $22_1$ and not the S polarization components II and III. Consequently, the light in the predetermined wavelength band containing R is separated into the P polarization component and the S polarization components. The image pickup element $22_2$ sequentially picks up images of the light of R, the light of G, and the light of B transmitted through the reception side polarization separation element $22_1$. The optical information obtained by the image pickup element $22_2$ is converted into a digital signal (image data) via a video signal circuit 32. An image operation device 33 subjects the resulting image data to, for example, the following image processing.

As described above, the P and S polarization components IV and III of scattering light are expected to have substantially the same light intensity. Thus, the intensity of the scattering light in the deep layer of the living body is determined from a P polarization component IV×2 obtained for the light in the predetermined wavelength band containing the wavelength band of R. The image operation device 33 subjects the light in the predetermined wavelength band which is shorter than 580 nm and which contains the wavelength bands of G and B, to image processing by, for example, adding image components for G and B together and outputting the result of the addition. Thus, the NBI with the B light and G light performed as the non polarization observation of the observation target can be carried out simultaneously with observation of the scattering condition based on the polarized light in the predetermined wavelength band which is longer than 580 nm and shorter than 700 nm and which contains the light of R.

Thus, the endoscope observation system in Example 4 enables simplification of the types and configurations of filters in the light source section used for the polarization observation and the non polarization observation. Furthermore, the endoscope observation system enables an increase in the diameters of the illumination optical system and the image pickup optical system to be prevented without the need for a mechanical structure for switching the polarization member. The endoscope observation system also allows the non polarization observation based on the visible light and the polarization observation in the yellow to red region and the infrared region to be performed using the same illumination optical system, while minimizing a decrease in the quantity of observation light for the observation based on the normal light. The other effects are almost the same as those of the endoscope observation system in Example 1.

In the above-described example, the rotary filter 12 is composed of the R, G and B filters 12a, 12b, and 12c arranged on the outer and inner peripheries thereof so that the rotary filter 12 is divided into the three pieces; the R, G, and B filters 12a, 12b, and 12c have the property of transmitting the respective wavelength bands of R, G, and B. However, the R filter 12a, serving as a polarization observation filter to transmit the wavelength band of R, may be located on the outer periphery. The G and B filters 12b and 12c, serving as a non polarization observation filters to transmit the light of G and the light of B, may be located on the inner periphery. In this case, the control section 31 may switch the position of each of the polarization observation filter and the non polarization observation filters on the illumination optical path, via a movement stage (not shown in the drawings) in response to a specification of each of the polarization observation mode and the non polarization observation mode (in this case, the NBI mode).

Also, according to the present invention, as an arrangement for allowing the NBI and the polarization observation to be simultaneously performed, the polarization separation wavelength band of the irradiation side polarization separation element $21_1$ and the reception side polarization separation element $22_1$ may be as narrow as that of G of the NBI. This configuration allows reflected light from the surface or the vicinity thereof to be removed from an image in the wavelength band of G in which vessels in a slightly deep layer are observed. This enables an increase in the accuracy with which the image with the wavelength band of G is separated from an image with the wavelength band of B describing capillary vessels in the vicinity of the surface.

Example 5

Figure 19:
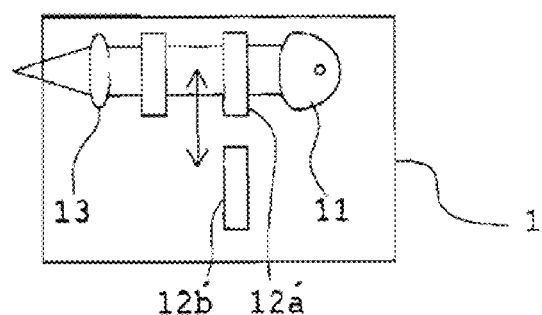
FIG. 19 is a schematic diagram showing the configuration of a light source section of an endoscope observation system in Example 5 of the present invention.
Figure 20A:
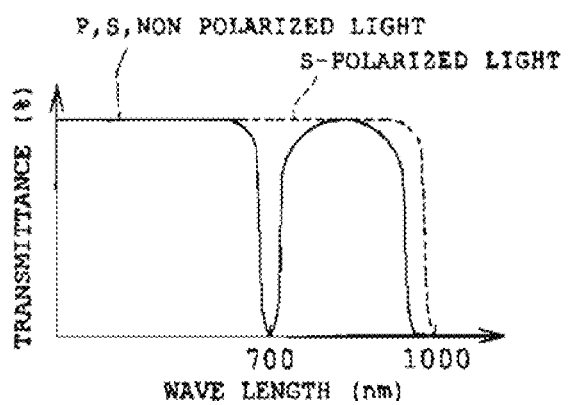
Figure 20B:
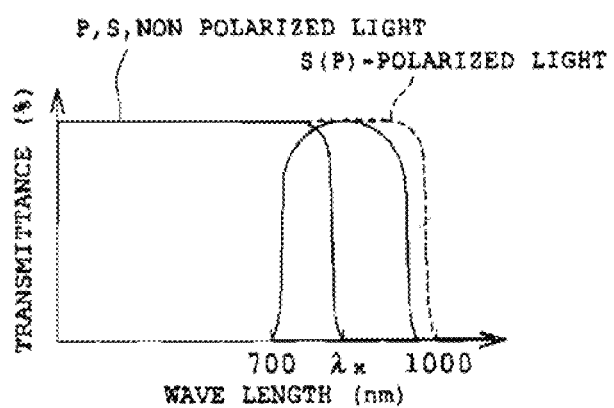
Figure 20C:
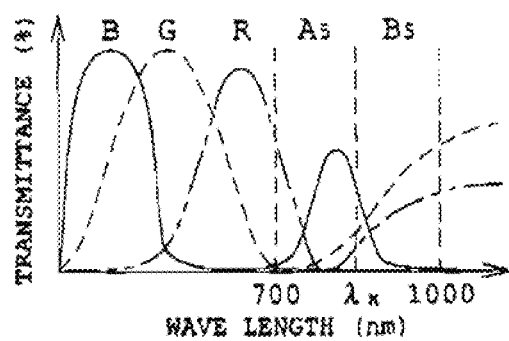

FIG. 19 is a schematic diagram showing the configuration of a light source section of an endoscope observation system in Example 5 of the present invention. FIGS. 20A, 20B, and 20C are graphs showing the characteristics of wavelength bands and optical elements for light used in an endoscope observation system in Example 5. FIG. 20A shows the transmission characteristics (a wavelength band used as illumination light in the polarization observation mode) of a filter for the polarization observation mode which is provided in a light source section, and the transmission characteristics (the wavelength bands of S-polarized light, P-polarized light, and non polarized light) of a polarization separation element provided in an illumination optical system. FIG. 20B shows a wavelength band used as illumination light in the polarization observation mode and the transmission characteristics (the wavelength bands of S-polarized light and P-polarized light) of a polarization separation element provided in an image pickup optical system. FIG. 20C shows the transmission characteristics of a mosaic filter on an image pickup element. The general configuration of the endoscope observation system in Example 5 is substantially the same as that of the endoscope observation system in Example 1 shown in FIG. 12 except for a light source section r. Here, only components different from those in Example 1 will be described. Furthermore, the configuration in FIG. 12 will be referenced as required.

The endoscope observation system in Example 5 adopts a simultaneous observation scheme. The endoscope observation system utilizes the infrared transmittance of the mosaic filter on an image pickup element $22_2$ to separate illumination light into two wavelength bands A and B belonging to the infrared wavelength band. The endoscope observation system thus obtains a polarized image and a non polarized image and determines the difference between the polarized image and the non polarized image. Specifically, as shown in FIG. 19, in the light source section 1, an infrared cut filter 12a' and a visible light cut filter 12b' are removably installed on the optical path in place of the rotary filter. The infrared cut filter 12a' has the property of interrupting light in the infrared wavelength band, which is longer than 700 nm and shorter than 1,000 nm, while transmitting light in the visible wavelength band, which is shorter than 700 nm. The visible cut filter 12b' has the property of interrupting the light in the visible wavelength band, which is shorter than 700 nm, while transmitting the light in the infrared wavelength band, which is longer than 700 nm and shorter than 1,000 nm.

The mosaic filter on the image pickup element $22_2$ has an R filter, a G filter, and a B filter. The R, G, and B filters have such transmission characteristics as shown in FIG. 20C. In the visible wavelength band, the transmission wavelength band of the B filter is separate from the transmission wavelength band of the R filter. Also in the infrared region of 700 to 1,000 nm, the transmission wavelength band of the B filter is substantially separate from the transmission wavelength band of the R filter as wavelength bands $A_5$ and $B_5$ located across a boundary wavelength λx.

Thus, the endoscope observation system in Example 5 enables the polarization observation to be performed in the infrared wavelength band of 700 to 1,000 nm. For the polarization observation, the endoscope observation system allows image information on reflected light from the cortical layer in the living body to be obtained by utilizing the transmission characteristics of the mosaic filter and using only image data obtained via the R filter and image data in the two separate wavelength bands $A_5$ and $B_5$ obtained via the B filter, and not image data obtained via the G filter.

A control section 31 drivingly controls a movement stage (not shown in the drawings) so that in the non polarization observation mode, the infrared cut filter (non polarization observation filter) 12a' is placed on the illumination optical path, whereas in the polarization observation mode, the visible light cut filter (polarization observation filter) 12b' is placed on the illumination optical path.

The irradiation side polarization separation element $21_1$ is composed of a prism type polarization beam splitter with a dichroic coat applied thereto. As shown in FIG. 20A, the irradiation side polarization separation element $21_1$ has the property of transmitting all of the P-polarized light, the S-polarized light, and the non polarized light for the illumination light from a light source section 1 in a predetermined wavelength band which is shorter than 700 nm and which contains the wavelength bands of R, G, and B. The irradiation side polarization separation element $21_1$ also has the property of transmitting only the S-polarized light for light in a predetermined wavelength band which is longer than 700 nm and shorter than 1,000 nm and which contains the above-described predetermined wavelength bands $A_5$ and $B_5$.

The reception side polarization separation element $22_1$ is composed of a prism type polarization beam splitter with a dichroic coat applied thereto. As shown in FIG. 20B, the reception side polarization separation element $22_1$ has the property of transmitting all of the P-polarized light, the S-polarized light, and the non polarized light for light in a predetermined wavelength band which is shorter than the above-described boundary wavelength λx and which contains the above-described predetermined wavelength band $A_5$ and the wavelength bands of R, G, and B, while transmitting only the S-polarized light for light in a predetermined wavelength band which is longer than the boundary wavelength λx and shorter than 1,000 nm and which contains the above-described predetermined wavelength band $B_5$. Furthermore, the reception side polarization separation element $22_1$ is located so as to rotate the transmitted light through 90 degrees so that the polarization direction of the polarization component (S-polarized light) transmitted in the polarization separation wavelength band (that is, the predetermined wavelength band which is longer than the boundary wavelength λx and shorter than 1,000 nm and which contains the above-described predetermined wavelength band $B_5$) is orthogonal to the polarization direction of the polarization component (S-polarized light) transmitted in the polarization separation wavelength band of the irradiation side polarization separation element $21_1$ (that is, the predetermined wavelength band which is longer than 700 nm and shorter than 1,000 nm and which contains the above-described predetermined wavelength bands $A_5$ and $B_5$) (this is not shown in the drawings).

Thus, for light entering the reception side polarization separation element $22_1$, that is, the light in the predetermined wavelength band which is longer than the boundary wavelength λx and shorter than 1,000 nm and which contains the above-described predetermined wavelength band $B_5$, the reception side polarization separation element $22_1$ transmits only the P-polarized light, which is perpendicular to the S-polarized light transmitted through the irradiation side polarization separation element $21_1$ (reference character P parenthesized in FIG. 20B indicates that the reception side polarization separation element $22_1$ actually transmits the P-polarized light in connection with the location). The remaining part of the configuration of the endoscope observation system is almost the same as that of the endoscope observation system in Example 1.

Observation using the endoscope observation system in Example 5 configured as described above will be described, when the polarization observation mode is specified, the control section 31 allows the movement stage (not shown in the drawings) to move and position the polarization observation filter (visible light cut filter 12b') on the illumination optical path. When a light source 11 emits light, the visible light cut filter 12b' interrupts light in the visible wavelength band, while transmitting light in the infrared wavelength band, which is longer than 700 nm and shorter than 1,000 nm. The light then enters a light guide $21_2$ via a condensing lens 13, upon entering the light guide $21_2$, the light in the infrared wavelength band, which is longer than 700 nm and shorter than 1,000 nm, enters the irradiation side polarization separation element $21_1$ via a lens $21_3$. In this case, the irradiation side polarization separation element $21_1$ has the property of transmitting only the S-polarized light for light in a predetermined wavelength band which is longer than 700 nm and shorter than 1,000 nm and which contains the predetermined wavelength bands $A_5$ and $B_5$. Thus, for the light in the predetermined wavelength band which is longer than 700 nm and shorter than 1,000 nm and which contains the predetermined wavelength bands $A_5$ and $B_5$, only the S polarization component passes through the irradiation side polarization separation element $21_1$. The light with the S polarization component transmitted through the irradiation side polarization separation element $21_1$ impinges on an observation target 5 via an illumination lens $21_4$.

Part of reflected light from the observation target 5 enters the reception side polarization separation element $22_1$ via an objective lens $22_3$ and an image forming lens $22_4$ of the image pickup optical system 22. In this case, the light reflected by the observation target 5 contains light with an S polarization component II reflected by the surface of the observation target 5 and having the same polarization condition as that of an irradiated S polarization component I, and light with an S polarization component III and a P polarization component IV with the polarization condition disturbed by scattering in the deep layer portion. The reception side polarization separation element $22_1$ has the property of transmitting all of the P-polarized light, the S-polarized light, and the non polarized light for the light in the predetermined wavelength band which is shorter than the above-described boundary wavelength λx and which contains the above-described predetermined wavelength band $A_5$ and the wavelength bands of R, G, and B. Thus, for the incident light in the predetermined wavelength band which is longer than 700 nm and shorter than λx and which contains the predetermined wavelength band $A_5$, all of the S polarization components II and III and the P polarization component IV pass through the reception side polarization separation element $22_1$.

The reception side polarization separation element $22_1$ also has the property of transmitting only the S polarization component for the light in the predetermined wavelength band which is longer than the boundary wavelength λx and shorter than 1,000 nm and which contains the predetermined wavelength band $B_5$. Furthermore, the reception side polarization separation element $22_1$ is located so as to rotate the polarization direction of the S-polarized light through 90 degrees which is transmitted through the reception side polarization separation element $22_1$ as described above. Thus, for the light in the predetermined wavelength band which is longer than the boundary wavelength λx and shorter than 1,000 nm and which contains the predetermined wavelength band $B_5$, only the P polarization component IV passes through the reception side polarization separation element $22_1$ and not the S polarization components II and III. Consequently, the light in the predetermined wavelength band $B_5$ is separated into the P polarization component and the S polarization components.

The image pickup element $22_2$ picks up images of the light in the predetermined wavelength band $A_5$ and the light in the predetermined wavelength band transmitted through the reception side polarization separation element $22_1$. At this time, the B and R filters in the mosaic filter, provided on the image pickup element $22_3$ substantially separate the infrared wavelength band of 700 to 1,000 nm into the two transmission wavelength bands across λx. Thus, the light in the predetermined wavelength band $A_5$ and the light in the predetermined wavelength band $B_5$ transmitted through the reception side polarization separation element $22_1$ are separated, via (the B and R filters in) the mosaic filter into light containing all of the S polarization components II and III and the P polarization component IV and light containing only the P polarization component IV in the predetermined wavelength band $B_5$.

The optical information obtained by the image pickup element $22_2$ is converted into a digital signal (image data) via a video signal circuit 32. An image operation device 33 subjects the resulting image data to, for example, the following image processing. As described above, the P and S polarization components IV and III of scattering light are expected to have substantially the same light intensity. Thus, the intensity of the scattering light in the deep layer of the living body is determined, from a P polarization component IV×2 obtained for the light in the predetermined wavelength band $B_5$, which is longer than the boundary wavelength $\lambda x$ and shorter than 1,000 nm. Furthermore, the S polarization component II is determined by subtracting the P polarization component IV×2 obtained for the light in the predetermined wavelength band $B_5$, which is longer than the boundary wavelength $\lambda x$ and shorter than 1,000 nm, from the non polarized image data made up of the S polarization components II and III and the P polarization component IV obtained for the light in the predetermined wavelength band $A_5$, which is longer than 700 nm and shorter than $\lambda x$. Consequently, the image of the S-polarized light reflected by the cortical layer in the living body can be exclusively calculated. The image only of the cortical layer can thus be observed via a monitor 4.

On the other hand, to allow for observation in the non polarization observation mode, the control section 31 allows the movement stage (not shown in the drawings) to move and position the non polarization observation filter (infrared cut filter 12a') on the illumination optical path. When the light source 11 emits light, light in the visible wavelength band, which is shorter than 700 nm and which contains R, G, and B, simultaneously passes through the infrared cut filter 12a' and enters the light guide $21_2$ via the condensing lens 13. Upon entering the light guide $21_2$, the light in the visible wavelength band, which is shorter than 700 nm and which contains R, G, and B, enters the irradiation side polarization separation element $21_1$ via the lens $21_3$. In this case, the irradiation side polarization separation element $21_1$ has the property of transmitting all of the P-polarized light, the S-polarized light, and the non polarized light for the light in the predetermined wavelength band which is shorter than 700 nm and which contains the wavelength bands of R, G, and B. Thus, the light in the visible wavelength band, which is shorter than 700 nm and which contains the wavelength bands of R, G, and B, passes through the irradiation side polarization separation element $22_1$ in the non polarized condition with the quantity of light prevented from being cut. The light of R, the light of G, and the light of B having passed through the irradiation side polarization separation element $22_1$ impinge on the observation target 5 via the illumination lens $21_4$.

Part of reflected light from the observation target 5 enters the reception side polarization separation element $22_1$ via the objective lens $22_3$ and the image forming lens $22_4$ of the image pickup optical system 22. In this case, the reception side polarization separation element $22_1$ has the property of transmitting all of the P-polarized light, the S-polarized light, and the non polarized light for light in a predetermined wavelength band which is shorter than $\lambda x$ and which contains the wavelength bands of R, G, and B. Thus, all of the non polarized light of R, the non polarized light of G, and the non polarized light of B pass through the reception side polarization separation element $22_1$ in the non polarized condition with the quantity of light prevented from being cut. The image pickup element $22_2$ sequentially picks up images of the light of R, the light of G, and the light of B transmitted through the reception side polarization separation element $22_1$.

The optical information obtained by the image pickup element $22_2$ is converted into a digital signal (image data) via the video signal circuit 32. The image operation device 33 subjects the resulting image data to image processing by, for example, adding together image components for R, G, and B obtained via the R, G, and B filters, respectively, making up the mosaic filter and outputting the result of the addition. Thus, a non polarization observation image is obtained with a possible decrease in the quantity of light prevented without the need to retract the polarization separation element $22_1$ from the optical path.

According to the endoscope observation system in Example 5, the light source section 1 need not divide polarization observation light into two wavelength bands. Thus, the filter configuration of the light source section 1 can be simplified. Furthermore, unlike an endoscope observation system based on a frame sequential scheme, the endoscope observation system in Example 5 completely eliminates the temporal deviation between images the difference between which is to be determined. This allows the difference to be more accurately determined. The other effects of the endoscope observation system in Example 5 are almost the same as those of the endoscope observation system in Example 1.

As is apparent from the above description, the endoscope observation system according to the present invention is useful in the fields of medical care, medical science, biology, and the like, which require the non polarization observation and polarization observation based on the visible light, NBI, AFI, or the like to allow observation of the appearance, shape, and the like of the interior of the living body and the condition of tissues in the living body.

What is claimed is:

1. An endoscope observation system configured to allow a polarized light-based observation image and a non polarized light-based observation image to be observed, comprising:
   a light source section generating a first type of illumination light for observation of the polarized light-based observation image and a second type of illumination light for observation of the non polarized light-based observation image, the first type of illumination light containing at least a first wavelength band, and the second type of illumination light being free from the first wavelength band;
   an irradiation side polarization separation element provided on an irradiation side optical path through which an observation target is irradiated with illumination light from the light source section, the irradiation side polarization separation element subjecting the first wavelength band in the first type of illumination light from the light source section to polarization separation so that light in the first wavelength band is separated into polarization components, and leaving another wavelength band outside the first wavelength band non-polarized;
   a single image pickup element that receives fed-back light derived from illumination light for acquiring an image;
   an image pickup lens component provided on a light reception side optical path through which light from the observation target is received, the image pickup lens component converging both of polarized light and non-polarized light from the observation target; and
   a light reception side polarization separation element provided on the light reception side optical path, the light reception side polarization separation element being configured so that, with respect to the light from the observation target converged by the image pickup lens component, only fed-back light having a predetermined polarization component, out of light in a second wavelength band, which is a part of the first wavelength band, is introduced to the image pickup element for imaging, while fed-back light in a third wavelength band, which exists outside of the second wavelength band, is introduced to the image pickup element for imaging irrespective of polarization condition, wherein, on an image pickup surface of the single image pickup element, a region on which the polarized light-based observation image is formed coincides with a region on which the non-polarized light-based observation image is formed.

2. The endoscope observation system according to claim 1, wherein the irradiation side polarization separation element performs polarization separation, in the first wavelength band of the illumination light from the light source section, by transmitting polarized light with the predetermined polarization component while reflecting polarized light with a polarization component other than the predetermined polarization component and, in a wavelength band outside the first wavelength band, exhibits the same transmission and reflection characteristics for both polarized light and non polarized light.

3. The endoscope observation system according to claim 1, wherein, in the first wavelength band, which forms a polarization separation wavelength band for the irradiation side polarization separation element, the irradiation side polarization separation element separates the illumination light into two orthogonal rays of linearly polarized light, and, in the second wavelength band, which is a polarization separation wavelength band for the reception side polarization separation element, the reception side polarization separation element separates the fed-back light into two orthogonal rays of linearly polarized light.

4. The endoscope observation system according to claim 3, wherein each of the irradiation side polarization separation element and the reception side polarization separation element is of a prism type.

5. The endoscope observation system according to claim 3, wherein the irradiation side polarization separation element and the reception side polarization separation element are arranged such that a polarization direction of a polarization component transmitted by the irradiation side polarization separation element in the first wavelength band is orthogonal to a polarization direction of a polarization component transmitted by the reception side polarization separation element in the second polarization wavelength band.

6. The endoscope observation system according to claim 2, wherein the irradiation side polarization separation element has a boundary wavelength of 580 nm or longer between the first wavelength band, which forms a polarization separation wavelength band therefor, and a transmission wavelength band therefor; and the reception side polarization separation element has a boundary wavelength of 580 nm or longer between the second wavelength band, which is a polarization separation wavelength band therefor, and a transmission wavelength band therefor.

7. The endoscope observation system according to claim 1, wherein the first type of illumination light used to observe the polarized light-based observation image comprises two different wavelength bands.

8. The endoscope observation system according to claim 7, further comprising an image processing device for calculating image information obtained by the image pickup element from an image of light in one of the two different wavelength bands and image information obtained by the image pickup element from an image of light in another of the two wavelength bands, so as to synthesize the image information into one image.

9. The endoscope observation system according to claim 7, wherein wavelengths of the first type of illumination light used to observe the polarized light-base observation image are equal to or longer than 580 nm, and substantially no illumination light used to observe the polarized light-based observation image is shorter than 580 nm.

10. The endoscope observation system according to claim 2, wherein, in the first wavelength band, which forms a polarization separation wavelength band for the irradiation side polarization separation element, the irradiation side polarization separation element separates the illumination light into two orthogonal rays of linearly polarized light, and, in the second wavelength band, which is a polarization separation wavelength band for the reception side polarization separation element, the reception side polarization separation element separates the fed-back light into two orthogonal rays of linearly polarized light.

11. The endoscope observation system according to claim 10, wherein each of the irradiation side polarization separation element and the reception side polarization separation element is of a prism type.

12. The endoscope observation system according to claim 10, wherein the irradiation side polarization separation element and the reception side polarization separation element are arranged such that a polarization direction of a polarization component transmitted by the irradiation side polarization separation element in the first wavelength band is orthogonal to a polarization direction of a polarization component transmitted by the reception side polarization separation element in the second wavelength band.

13. The endoscope observation system according to claim 2, wherein the first type of illumination light used to observe the polarization light-based observation image comprises two different wavelength bands.

14. The endoscope observation system according to claim 13, and further comprising an image processing device for calculating image information obtained by the image pickup element from an image of light in one of two different wavelength bands and image information obtained by the image pickup element from an image of light in another of the two wavelength bands, so as to synthesize the image information into one image.

15. The endoscope observation system according to claim 13, wherein the wavelengths of the first type of illumination light used to observe the polarized light-based observation image are equal to or longer than 580 nm, and substantially no illumination light used to observe the light-based observation image is shorter than 580 nm.

16. The endoscope observation system according to claim 4, wherein each of the irradiation side polarization separation element and the reception side polarization separation element is constructed of a prism-type polarization beam splitter with a dichroic coating applied thereto.

17. The endoscope observation system according to claim 11, wherein each of the irradiation side polarization separation element and the reception side polarization separation element is constructed of a polarization beam splitter with a dichroic coating applied thereto.

* * * * *